(12) United States Patent
Suffin

(10) Patent No.: US 7,754,190 B2
(45) Date of Patent: *Jul. 13, 2010

(54) METHOD FOR DETERMINING DRUG EFFECTS USING QUANTITATIVE EEG

(75) Inventor: Stephen Suffin, Sherman Oaks, CA (US)

(73) Assignee: CNS Response, Inc., Aliso Viejo, CA (US)

( * ) Notice: Subject to any disclaimer, the term of this patent is extended or adjusted under 35 U.S.C. 154(b) by 13 days.

This patent is subject to a terminal disclaimer.

(21) Appl. No.: 10/602,077

(22) Filed: Jun. 23, 2003

(65) Prior Publication Data

US 2004/0059241 A1   Mar. 25, 2004

Related U.S. Application Data

(60) Division of application No. 09/501,149, filed on Feb. 9, 2000, now Pat. No. 6,622,036, which is a continuation-in-part of application No. 09/148,591, filed on Sep. 4, 1998, now abandoned.

(60) Provisional application No. 60/058,052, filed on Sep. 6, 1997.

(51) Int. Cl.
*A61K 49/00*       (2006.01)

(52) U.S. Cl. ............... 424/9.2; 424/1.11; 424/1.65; 424/9.1; 600/544; 600/545

(58) Field of Classification Search ............... 424/1.11, 424/1.65, 9.1, 9.2
See application file for complete search history.

(56) References Cited

U.S. PATENT DOCUMENTS

| 4,753,246 A | * | 6/1988 | Freeman | 600/544 |
| 6,067,467 A | * | 5/2000 | John | 600/544 |
| 6,622,036 B1 | * | 9/2003 | Suffin | 600/544 |

OTHER PUBLICATIONS

Cohen et al (Neuropsychopharmacology, 1993, vol. 8, No. 4, pp. 365-370).*
Wenk et al (The Journal of Neuroscience, Oct. 1994, vol. 14, No. 10, pp. 5986-5995).*

* cited by examiner

*Primary Examiner*—D L Jones
(74) *Attorney, Agent, or Firm*—Medlen & Carroll, LLP

(57) ABSTRACT

Neurophysiologic information such as quantitative electroencephalography (QEEG) is used in a method for classifying, diagnosing, and treating physiologic brain imbalances. Neurophysiologic information is also used to guide sample selection in clinical tests for psychopharmacologic drug candidates. Finally, neurophysiologic information is used for remotely assessing and treating patients with physiologic brain imbalances.

10 Claims, 15 Drawing Sheets

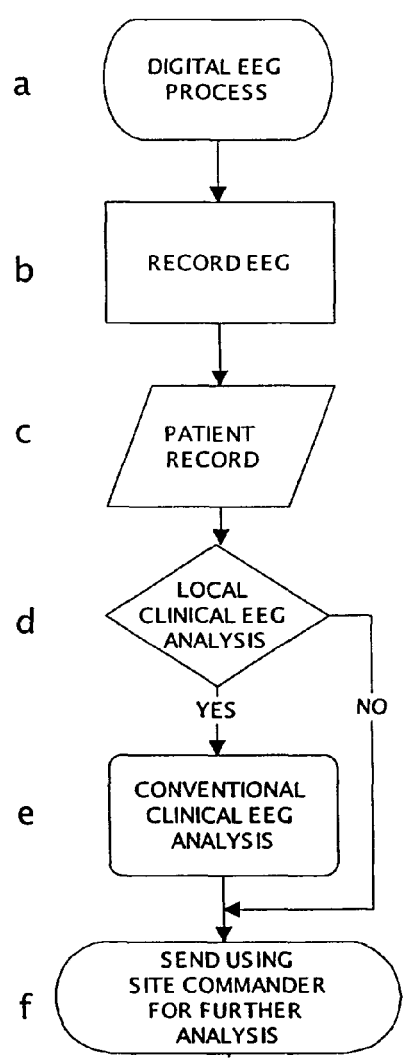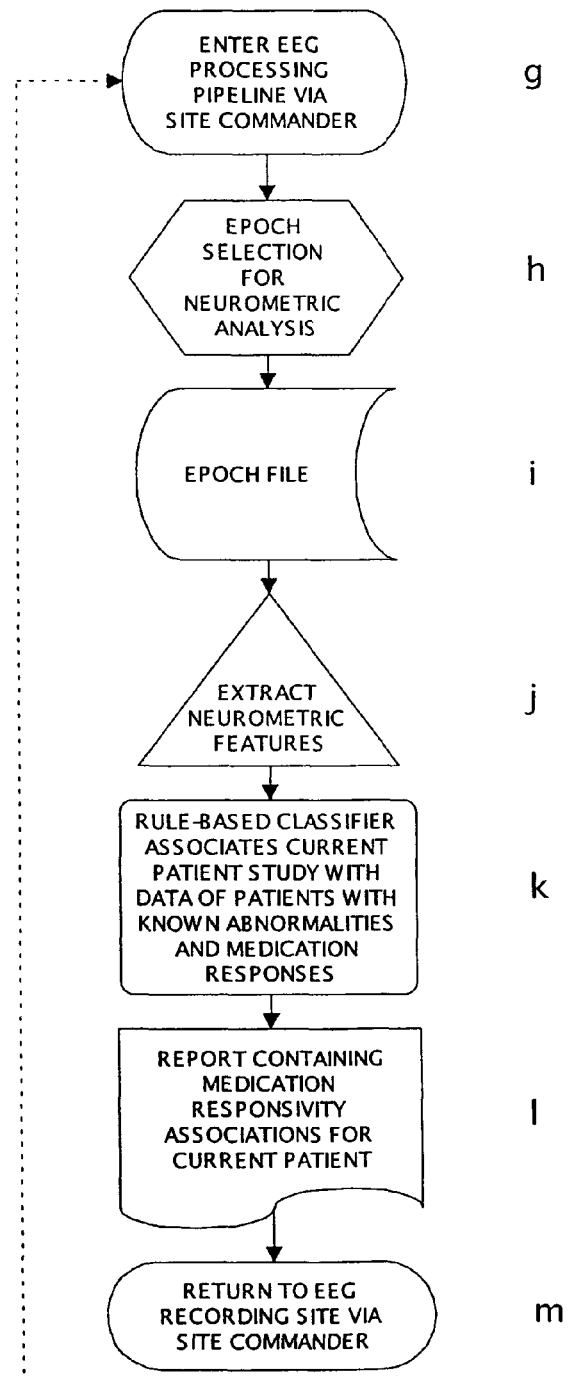

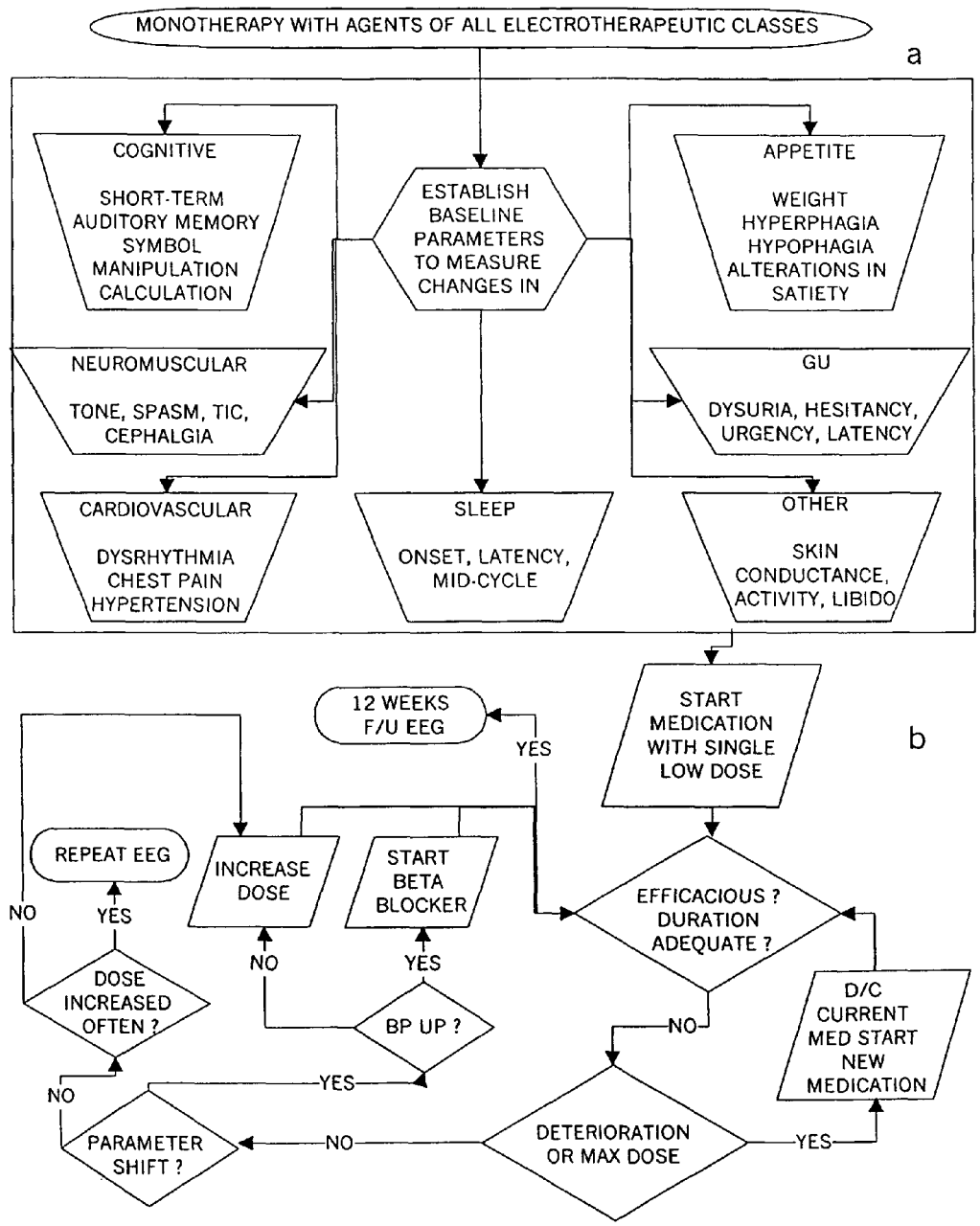

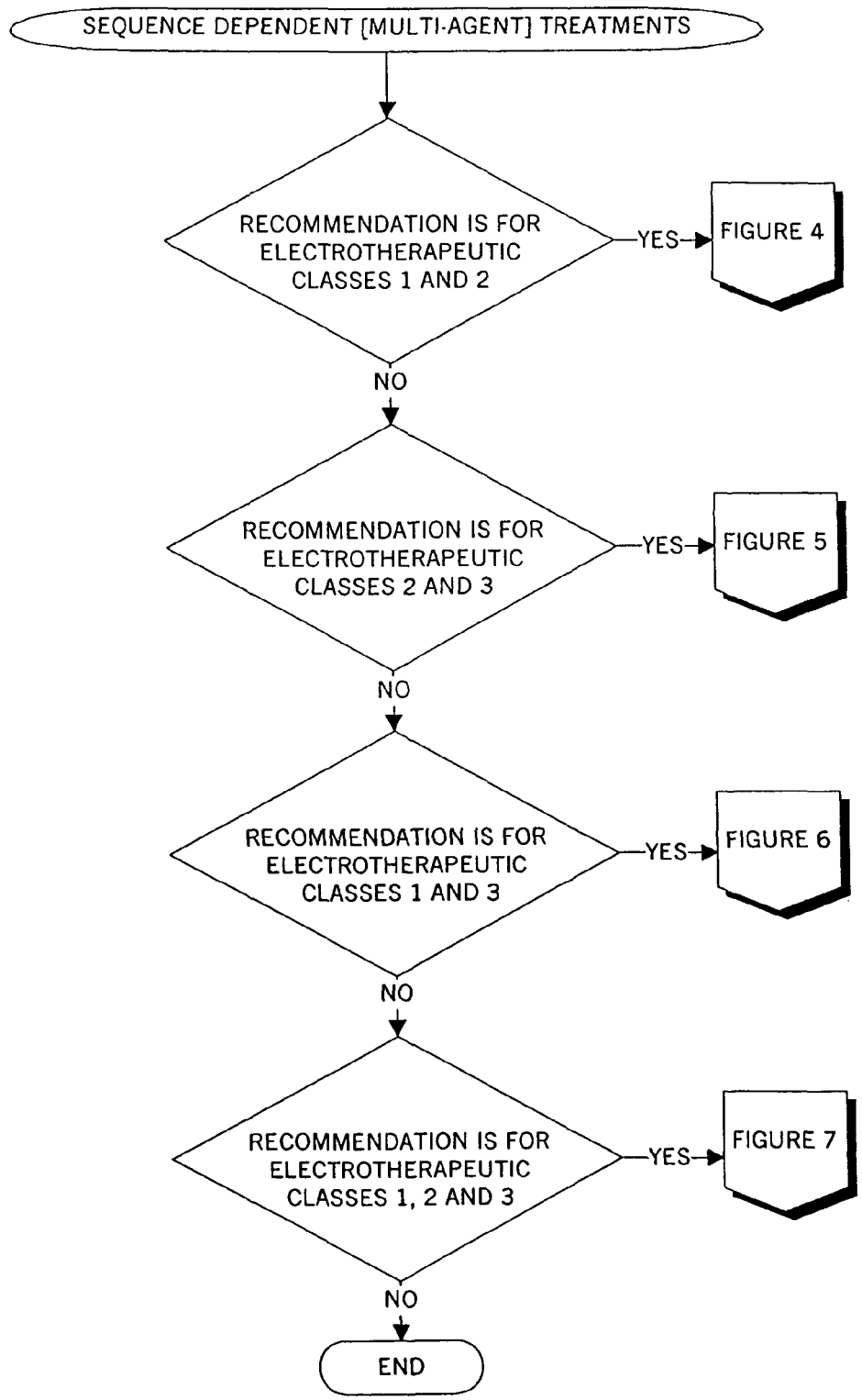
FIGURE 3.2

METHOD FOR DETERMINING DRUG EFFECTS USING QUANTITATIVE EEG

This application is divisional of application Ser. No. 09/501,149, filed Feb. 9, 2000, now issued as U.S. Pat. No. 6,622,036, which is a continuation-in-part of application Ser. No. 09/148,591 Sep. 4, 1998 (now abandoned), which is a continuation of Application No. 60/058,052, filed Sep. 6, 1997.

BACKGROUND OF THE INVENTION

Many researchers continue to attempt to employ neurophysiologic techniques, such as electroencephalography (EEG), magnetic resonance imaging (MRI), functional magnetic resonance imaging (FMRI), positron emission tomography (PET), single photon emission computerized tomography (SPECT), as well as others, to guide therapeutic outcome in psychiatry. For example, the neurophysiologic technique of EEG measures the electrical activity of the brain as a function of time varying spontaneous potentials (SP) through a number of electrodes placed at standard locations on the scalp. The neurophysiologic information obtained through EEG analysis is recorded as sets of traces of the amplitude of SP referenced over time for scalp electrodes that are referenced electrically. This analog EEG information can then be visually analyzed and interpreted for signal abnormalities.

In the 1970's, quantitative analysis of the EEG signal provided rapid easy access to measurements that extended the EEG method beyond qualitative visual detection of signal abnormality. Quantitative EEG (QEEG) studies involve the multi-channel acquisition, processing, and analysis of brain activity often but not exclusively by computers. An example of an EEG/QEEG instrument is the Easy Writer II system, available from Caldwell Laboratories, Inc. (Kennewick, Wash.).

In one version of EEG/QEEG recordings, nineteen or more electrodes are commonly placed at standard locations on the scalp using the International 10/20 Placement System. A multi-channel recording of the brain's activity in an awake, eyes-closed, or "background" state is then recorded and analyzed often by use of Fast Fourier Transform (FFT) signal processing. Signal processing of the raw EEG permits measurement and quantification of multiple characteristics of brain electrical activity. In this process, artifacts due to muscle or eye movement or environmental noise are rejected, leaving only valid information suitable for further analysis.

Although technical and methodological guidelines for versions of EEG/QEEG extraction have been presented, studies that do not observe these essential guidelines are common. In addition to guideline non-conformance, the practice of ignoring the composite nature of psychiatric imbalances is commonplace. As a result, typical EEG/QEEG findings have not always been repeatable, and use of these versions of QEEG in psychiatric assessment and treatment is minimal.

Current behavioral definitions of psychiatric disorders do not correlate well with response patterns to medical treatment. Since psychiatric imbalances are behaviorally defined, they do not demonstrate a consistent relation with individual neurophysiological information, such as from EEG/QEEG or other neurophysiological techniques such as MRI, FMRI, PET, SPECT or other related techniques. However, if neurophysiological information were used as the independent variable and medication response is analyzed as the dependent variable, a connection between neurophysiology and the clinical outcome of treatment may be observed.

There is a need to develop clinical methods for using neurophysiological information as an independent variable and medication response as the dependent variable in order to probe the connection between neurophysiology and treatment outcome. Given such methods, the relationship between observed neurophysiologic abnormality, neurophysiologic intervention, and neurophysiologic treatment outcome in a given patient can be gauged.

There also is a need to develop a method for comparing quantified neurophysiologic information so that pattern differences between individual patients and reference groups can be catalogued and further, for classifying the neurophysiologic information of symptomatic patients according to anticipated treatment response and outcome measures.

There is a further need to develop a method for treating physiologic brain imbalances using neurophysiologic information. Supplemental to these treatment-associated needs, there is a need to develop a method for guiding clinical testing for new chemical, electrical, magnetic other interventions to treat physiologic brain imbalances, and for identifying new uses for known interventions.

Finally, there is a need to develop a method for the remote assessment and treatment of physiologic brain imbalances using neurophysiologic information.

SUMMARY OF THE INVENTION

These and other needs are met by the present invention, which is directed to a method for classifying and treating physiologic brain imbalances. The method involves using neurophysiologic techniques to obtain a set of analytic brain signals from a patient. A set of digital parameters is determined from this set of analytic brain signals. The analytic brain signals employed in the present invention are collected from neurophysiologic instruments that collect and store neurophysiologic data such as EEG/QEEG signals, MRI signals, PET signals, SPECT signals, and any combination or variation thereof. The digital parameters generated from these analytic signals can be quantitatively mapped to various therapy responsivity profiles.

More particularly, the method of the invention employs neurophysiologic information for assessing, classifying, analyzing and generating treatment recommendations for physiological brain imbalances. The invention is based upon the discovery that neurophysiologic information can be used as an independent variable to identify physiologic brain imbalances.

According to the invention, the analytic brain signals and preferred quantified parameters for a patient that are obtained using neurophysiologic techniques are compared to aggregate neurophysiologic information contained in databases relating to "asymptomatic" and "symptomatic" reference populations. This process of comparison is used to make treatment recommendations. A catalogue of physiological deviations in the neurophysiologic information of patients with psychiatric disturbance is constructed according to the invention by comparing individual patient neurophysiologic information, preferably quantified neurophysiologic information, with the neurophysiologic information of reference populations of symptomatic and asymptomatic individuals. A set of multivariable neurophysiologic outcome measurements is developed to gauge deviation magnitudes and to establish pattern differences between individual patients and reference groups. Treatment response patterns are then correlated according to the invention as a dependent variable with this information, as discussed in detail below. It has been discovered that this correlation provides a strong connection to successful outcomes for clinical treatment of afflicted patients.

In one aspect, the present invention is directed to a method for classifying and cataloguing physiologic brain imbalances using neurophysiologic information, and more preferably, quantified neurophysiologic information, relative to a reference population of asymptomatic persons. Physiological deviation from normal functioning, or pathophysiology, defines a biologic model that is the basis of this method. According to the method, physiological deviation is an independent variable that organizes and guides the selection of physiologic therapy regimes to treat disease.

In another aspect, the present invention is directed to a method for assessing and treating physiologic brain imbalances using quantified neurophysiologic information such as EEG/QEEG or SPECT. This aspect of the present invention uses physiological criteria to guide selection of treatment modalities to yield improved therapeutic outcomes. In the method, quantified multivariable neurophysiologic outcome measurements that have been classified as abnormal based on comparison to the quantified multivariable neurophysiologic outcome measurements of a normal or asymptomatic population is submitted for further neurophysiologic analysis using an Outcomes Database for comparison. This Outcomes Database contains neurophysiologic information from symptomatic individuals who exhibit clinical manifestations of psychiatric imbalances. Individual patient quantified neurophysiologic information is matched to the quantitative neurophysiologic information of individuals with known medication response outcomes to provide a profile of the physiological state of the patient's brain function. This profile information is associated with the outcome of specific treatment modalities for this group of patients. Using these associations, a probabilistic treatment recommendation is made.

In still another aspect, the present invention is directed to a method for selecting individual human participants for clinical drug trials of new compounds for treating physiologic brain imbalances, as well as to a method for inferring novel uses for known compounds in treating physiologic brain imbalances.

In another aspect, the present invention is directed to a method for determining central nervous system (CNS) application of new drugs by determining the effect of the drug upon the neurophysiologic information of a human participant in a clinical trial. Preferably this method involves comparison of the effects of the new drug upon the participant's neurophysiologic profile to a data base of known profile effects caused by administration of drugs known to have effects on the neurophysiologic profile.

In still another aspect, the present invention is directed to a method for the remote assessment and treatment of physiologic brain imbalances using quantified neurophysiologic information. In the method, an electronic link is established between a medically under-served area, or "remote location" and a center of neurophysiologic expertise, or "central processing location." In the context of assessing and treating physiologic brain imbalances, the electronic link could be between a physician with digital neurophysiologic capabilities and a quantified neurophysiologic information processing center. In short, in the remote assessment and treatment method, a patient's quantified neurophysiologic information is transmitted electronically without loss of resolution to a quantified neurophysiologic information analysis center. The quantified neurophysiologic information is then compared to database information to suggest treatment strategies.

In a preferred aspect of the invention, the quantified neurophysiologic information is collected and analyzed using electroencephalographic (EEG) or single photon emission computerized tomography (SPECT) techniques and more preferably using quantitative electroencephalographic (QEEG) or quantitative SPECT techniques.

The invention is also directed to software techniques, computer software, computer programming techniques, and algorithms for conducting the neurophysiologic analysis, remote transmission, and treatment methods described above.

According to the present invention, it is preferred that the neurophysiologic information is quantified neurophysiologic information and is obtained by a neurophysiologic technique selected from the group consisting of electroencephalography, magnetic resonance imaging, positron emission tomography, single photon emission computerized tomography and any combination thereof. Also according to the present invention, it is preferred that the neurophysiologic information is quantified neurophysiologic information and is obtained by a neurophysiologic technique of electroencephalography. Finally according to the present invention, it is preferred that the neurophysiologic information is quantified neurophysiologic information and is obtained by a neurophysiologic technique of single photon emission computerized tomography. These preferences apply to all the embodiments and claims in this application.

BRIEF DESCRIPTION OF THE FIGURES

FIG. 1 depicts an algorithm for local and remote clinical assessment of physiologic brain imbalances, particularly as relating to the technique of EEG/QEEG.

FIG. 3.1 depicts an algorithm for making monotherapy, or single drug therapy, recommendations using the method of the present invention.

FIG. 3.2 further depicts the process of multi-drug therapy using the method of the present invention.

DETAILED DESCRIPTION OF THE INVENTION

Figure 2:
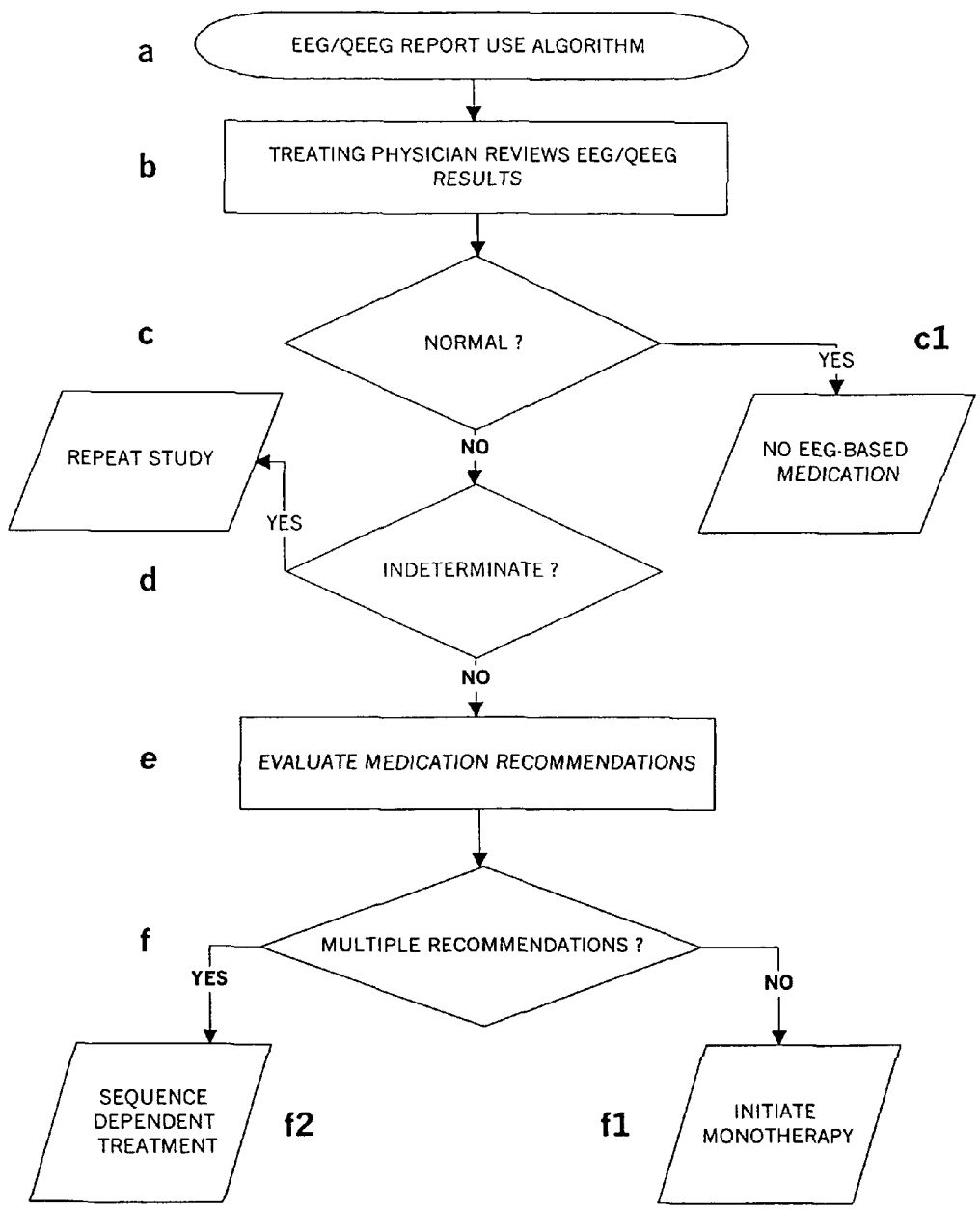
FIG. 2 depicts an algorithm for using neurophysiologic information, preferably EEG/QEEG information, to assess physiologic brain imbalances and make treatment recommendations.
Figure 4:
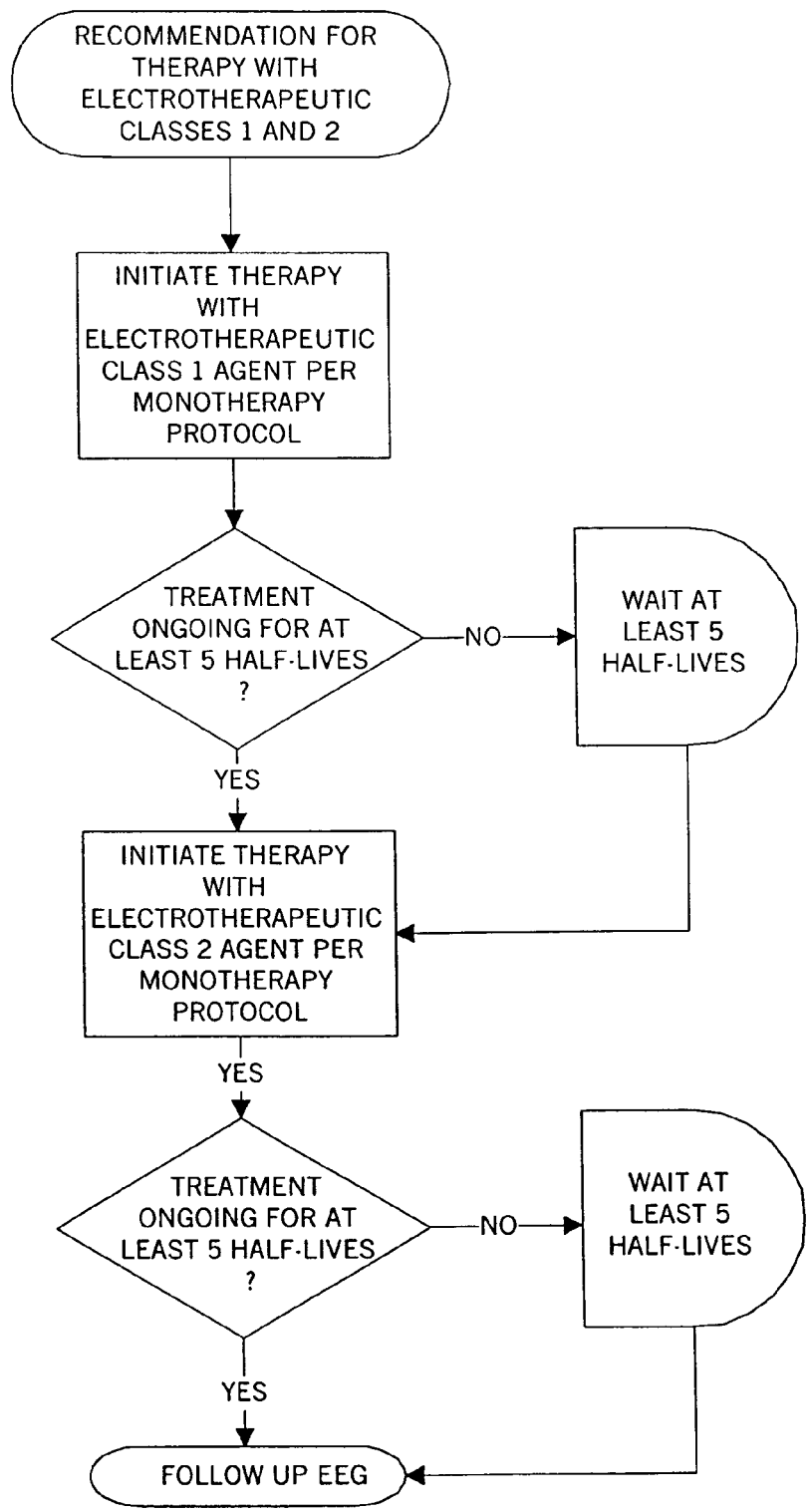
FIG. 4 depicts an algorithm for making multiple agent therapy recommendations using the method of the present invention for drugs that are in electrotherapeutic classes 1 and 2.

The present invention relates to a method for classifying physiologic brain imbalances using neurophysiologic information, more preferably quantified neurophysiologic information, which includes, but is not limited to information derived from EEG/QEEG, MRI, FMRI, PET, SPECT, as well as any other method that measures neurophysiologic brain function. Preferably, the method uses EEG or SPECT, and more preferably, QEEG or quantitative SPECT. The present invention also relates a method for comparing quantified neurophysiologic information to establish pattern differences between individual patients and asymptomatic or symptomatic reference populations. The present invention additionally relates a method for assessing and treating patients with physiologic brain imbalances using neurophysiologic outcome measurements, preferably multivariate neurophysiologic outcome measurements, to guide choice of treatment modality. The present invention additionally relates a method for guiding clinical testing for new drugs to treat physiologic brain imbalances, and for identifying new uses for known drugs. Finally, the present invention relates a method for the remote assessment and treatment of physiologic brain imbalances using neurophysiologic techniques such as QEEG or quantitative SPECT.

DEFINITIONS

The terms used in this specification have the meanings and preferred embodiments as provided unless specified otherwise.

"Neurophysiologic information" is the information obtained from the measurement of electronic or chemical impulses caused by brain function, using the techniques of EEG/QEEG, MRI, FMRI, PET, SPECT, and the like.

"Quantified neurophysiologic information" is neurophysiologic information that has been analyzed to determine one or more numeric scale parameters characterizing the neurophysiologic information. For example quantified electroencephalography (QEEG) involves any quantification of a qualitative EEG spectrum including but not limited to measurement of the peak heights and relationships of paroxysmal and nonparoxysmal events in the EEG spectrum. An embodiment of QEEG is the digitized, fast Fourier transformed analysis of multichannel recordings from the nineteen or more electrodes placed according to the international 10/20 placement system described in the "Background of the Invention".

A "paroxysmal event" is a brief sudden disturbance in the background EEG, often consisting of short duration spikes and waves, which are often but not always accompanied by a sudden voluntary or involuntary muscle movement.

A "nonparoxysmal event" is an artifact-free background EEG, the artifacts being the short duration spikes and waves indicative of a paroxysmal event.

"QEEG" means quantitative electroencephalography either of the broad scope understood by the term "quantified neurophysiologic information" or by the specific embodiment obtained by digitized fast Fourier transform analysis. This term is used in both senses in this application, the choice being indicated by the context of the discussion or by the use of the term "general QEEG" to indicate the broad scope term or by the term "FFT QEEG" to indicated the specific embodiment.

"Neurometric analysis" is the quantification of the brain's electrophysiological function referenced to a group of "normal" or asymptomatic age-matched controls using quantified neurophysiologic information.

A "physiologic brain imbalance" means a quantifiable deviation in the neurophysiologic functioning of a patient as compared to a reference population of "normal" or asymptomatic individuals or groups. "Normal" or "asymptomatic" individuals or groups are those who do not exhibit behavioral or physiologic indicia of brain imbalance.

"Multivariate outcome measurements" are quantitative output measurements collected from combinations of univariate neurophysiologic measurements collected from various regions of the brain. For one of the preferred techniques, the QEEG technique, multivariate outcome measurements are collected from combinations of QEEG electrodes for each frequency band of the EEG spectrum. For the QEEG technique, the multivariate measurements of the present invention are derived from measurement of absolute power ($\mu V^2$) in each band of the EEG spectrum; relative power (percentage power in each channel) in each band of the EEG spectrum; coherence (a measure of synchronization between activity in two channels) in each band of the EEG spectrum; and symmetry (the ratio of power in each band of the EEG spectra between a symmetrical pair of electrodes).

"Behavioral diagnosis" is diagnosis of mental illness based on behavioral indicia, as observed by psychiatrists and other health care professionals and codified by the Diagnostic Statistical Manual (DSM), now in its fourth edition (American Psychiatric Association. Diagnostic and Statistical Manual of Mental Imbalances. *DSM IV, Fourth Edition*. Washington, D.C.: American Psychiatric Association), or the International Classification of Diseases (ICD) (posted at http://cedr.l-bl.gov/icd9.html, last visited Jan. 26, 2000) or similar classification systems.

"Behaviorally defined forms of mental illness" are forms of mental illness that manifest themselves in behavioral pathologies and abnormalities as defined by the DSM or ICD.

"Behavioral indicia of physiologic brain imbalances" are the diagnostic indicators of psychiatric or neurologic disorders as defined by the DSM or ICD.

"Behaviorally diagnosed brain pathologies" are physiologic brain imbalances that manifest themselves in the behaviorally defined forms of mental illness.

"Non-behaviorally diagnosed brain pathologies" are physiologic brain imbalances that do not manifest themselves in the behaviorally defined forms of mental illness but nonetheless are observable by physiological analysis or long term psychotherapy demonstrating a thought disturbance for example, a paranoia.

"Z scores" are uniform differential probability scores. Z-scores are calculated by dividing the difference between an observed value and the mean for the expected "normal" value by the standard deviation of the expected "normal" value.

A "responsivity profile" is a treatment response profile that relates to how patients with physiologic brain imbalances respond to various methods of treatment.

A "treatment modality" is a way of treating a physiologic brain imbalance.

An "electrotherapeutic drug class" is a grouping of drugs based on a designated neurophysiologic effect. For the preferred QEEG technique, drugs are grouped according to their effects on quantitative multivariable outcome measurements collected from combinations of EEG electrodes for each region of the EEG spectrum.

I. Classifying and Comparing Quantified Neurophysiologic Information to Establish Differences Between Individual Patients and Reference Groups Neurophysiologic information, preferably EEG information, gives rise to objective, precise, and statistically useful information about the brain, and to the abnormal or pathologic brain functions that may manifest themselves in the behavioral symptoms, or "indicia" of mental or neurological illness. EEG/QEEG allows for the comparison of individual patient quantified neurophysiologic information with quantified neurophysiologic information from a reference population.

Quantified neurophysiologic information distinguishes medication effects on brain function. Medications produce differential changes in the quantified neurophysiologic information that are measurable across physiologic brain imbalances, defined as psychiatric or neurological syndromes. Based in part on observations of medication effects on neurophysiologic information, general classifications have been developed that group psychiatric or neurological imbalances based on quantified neurophysiologic information such as EEG/QEEG information. Classification methods have been developed that group psychotropic or neurotropic medications according to EEG/QEEG changes in "normal" or asymptomatic individuals. In psychiatry, for example, observation of abnormal patterns of behavior is the independent variable that is primarily used to catalogue and diseases of the brain.

Without neurophysiological information regarding physiological deviations in brain function, drug treatment of psychiatric and neurologic imbalances has proven difficult. The well-known heterogeneity of medication response associated with major psychiatric illnesses supports the hypothesis that variable neurophysiology is involved.

In contrast, the classifying method of the present invention involves the comparison of individual patient neurophysiologic information, preferably quantified neurophysiologic information, with neurophysiologic information, preferably quantified neurophysiologic information, drawn from reference populations of asymptomatic and symptomatic individuals. The use of multivariable measurements based on neurophysiologic information, preferably quantified neurophysiologic information, described below, provides a way to determine if the use of a treatment modality is likely to improve the clinical status of a patient.

According to the invention, the classifying and comparing method includes an exploration of clinically relevant physiologic features that characterize brain imbalances. Of the quantitative neurophysiologic technologies available such as MRI, FMRI, PET, and SPECT as well as others, the neurophysiologic method of EEG/QEEG is a practical clinical tool because it is non-invasive, includes a well-replicated normative database, has a potential for broad distribution, and is easily adapted to a variety of clinical settings.

Preliminary to the practice of the invention EEG information is collected from electrodes placed at standard locations on a patient's scalp using, by convention, the International 10/20 System for electrode placement. The information is digitized and then undergoes fast Fourier transform (FFT) signal processing to yield a QEEG spectrum. In addition to quantifying the power at each frequency averaged across the QEEG spectrum for each electrode, FFT signal processing of the raw EEG signal provides measurement and quantification of other characteristics of brain electrical activity.

The QEEG spectrum is divided into four frequency bands: delta (0.5-3.5 Hz); theta (3.5-7.5 Hz); alpha (7.5-12.5 Hz); and beta (12.5-35 Hz). The spectrum also includes the results from each of the EEG electrodes represented as quantitative output measurements for each frequency band. These include absolute power in each band ($\mu V^2$); relative power in each band (percentage power in each channel); coherence (a measure of synchronization between activity in two channels); and symmetry (the ratio of power in each band between a symmetrical pair of electrodes).

Although not intended as a limitation of the invention, the relationship between these univariate measurements and brain activity is believed to be as follows. Absolute power is the average amount of power in each frequency band and in the total frequency spectrum of the artifact-free EEG information from each electrode, and is believed to be a measure of the strength of brain electrical activity. Relative power is the percentage of the total power contributed for a respective electrode and a respective frequency band, and is believed to be a measure of how brain activity is distributed. Symmetry is the ratio of levels of activity measured between corresponding regions of the two brain hemispheres in each frequency band and is believed to be a measure of the balance of the observed brain activity. Coherence is the degree of synchronization of electrical events in given regions of the two hemispheres and is believed to be a measure of the coordination of the observed brain activity. According to the invention, it is believed that these four univariate measures of EEG information can be used to characterize physiological brain imbalances, which manifest themselves in various behavioral pathologies.

Using these univariate measures, univariate Z scores, or uniform differential probability scores are calculated. Univariate Z scores for each quantitative output measurement for each electrode are calculated, by dividing the difference between an observed value and the mean for the expected "normal" value by the standard deviation of the expected "normal" value. The "normal" values are provided by a commercially available database such as NxLink (biof.com/nx-link; last visited Jan. 25, 2000). The Z transformation process scales all relevant information into units of probability (or units proportional to probability), yielding a uniform scale in all dimensions which can simplify further comparisons and evaluations of relationships between features.

An EEG/QEEG instrument, such as the Spectrum 32, manufactured by Caldwell Laboratories, Inc. (Kennewick, Wash.), can readily execute these univariate neurometric Z transformations. This instrument contains age-defined norms in databases of age regression expressions defining a distribution of features as functions of age in a normal population. The instrument extracts from the database the mean value and the standard deviation to be expected for each feature of a group of "normal" subjects the same age as a patient. It automatically evaluates the difference between the value of each feature observed in the patient and the age-appropriate value predicted by the database age regression expressions. The instrument subsequently evaluates the probability that the observed value in the patient belongs to the "normal" group, taking into account the distribution of values in the "normal" group. A completely analogous process can be accomplished using a family of different digital EEG machines and commercially available neurometric software, such as that available from NxLink, Inc.

IA. Profile of a Patient's Neurophysiologic Information

Preliminary to the practice of the method of the present invention, a profile of a patient's univariate QEEG data is constructed. The purpose of the profiling step is to collect univariate Z scores. This method of the present invention includes the steps, depicted in FIG. 1. FIG. 1 summarizes the acquisition and analysis process for both conventional (or on-site) and remote (or off-site) treatment plans. As is described in a later section, remote treatment involves the transmittal of digitized EEG information from a "remote" clinical setting to a center of expertise.

As a preliminary step to the method of the present invention, an ordinary EEG is obtained by acquiring and recording a patient's digitized EEG (steps a-b). Univariate neurophysiologic features are extracted from the digitized EEG (step h-j). These univariate neurophysiologic features include measures of absolute power, relative power, coherence, and symmetry for each of the electrodes of the International 10/20 System that are placed on a patient's scalp are derived. These univariate neurometric features are compared to QEEG information collected from individuals who are clinically assessed to be asymptomatic for physiologic brain imbalances. A Z score is computed for each measure.

As indicated earlier, the Z scores are uniform differential probability scores that represent deviations from the composite normal QEEG information of a commercially available neurometric database, such as the NxLink database mentioned above. The neurometric database is constructed from the QEEGs of individuals from 6 to 92 years of age and incorporates information from every electrode used by convention in the international 10/20 System for electrode placement. The database contains over 1000 quantitative univariate EEG measures. The Z score that is obtained by comparing an individual patient's QEEG information with the information for the reference asymptomatic population represents the patient's statistical deviation from the reference-asymptomatic database. That is, if a patient's Z score for a particular measure does not statistically deviate from the reference asymptomatic population, the patient would be determined to be "asymptomatic" for that measure. However, if a patient's Z score is found to statistically deviate from the reference population for a particular measure, the patient would be determined to be symptomatic for that measure.

IB. Developing QEEG Multivariables

A preliminary step to the method of the invention involves the extraction of univariate measures from a patient QEEG and subsequent comparison to composite information from the asymptomatic reference population (cf., Step j of FIG. 1). However, according to the invention, multivariate measures based upon the univariate measurements are made. To this end, step j of FIG. 1 additionally involves the extraction of multivariate measures from a patient's EEG/QEEG. The multivariables described in Chart 1.1 are formulated according to the method of the present invention for assessing and making treatment recommendations. The set of multivariate features summarized in Chart 1.1 were constructed using neurophysiologic descriptors that successfully compress the univariate data described above without distorting the informational content of the univariate measures. Although it is not intended to be a limitation of the invention, it is believed that the analysis of multivariable deviations from the statistical normal set of signals provides a precise system for recognition of a multitude of physiologic brain imbalances that are unrecognized from univariate signal analysis. Chart 1.2 lists the EEG electrodes or pairs of electrodes from which the numeric magnitude of each of the multivariable descriptors are determined. These electrodes or pairs of electrodes are identified according to their names under the International 10/20 electrode locating system.

CHART 1.1

Multivariate QEEG Descriptors

| Name | Description | Name | Description |
|---|---|---|---|
| RMAD | Relative power Monopolar Anterior Delta | CABL | Beta - Left |
| RMPD | Posterior Delta | CABR | Beta - Right |
| RMAT | Anterior Theta | QMAD | Frequency Monopolar Anterior Delta |
| RMPT | Posterior Theta | QMPD | Posterior Delta |
| RMAA | Anterior Alpha | QMAT | Anterior Theta |
| RMPA | Posterior Alpha | QMPT | Posterior Theta |
| RMAB | Anterior Beta | QMAA | Anterior Alpha |
| RMPB | Posterior Beta | QMPA | Posterior Alpha |
| CEAD | Coherence interhemispheric Anterior Delta | QMAB | Anterior Beta |
| CEPD | Posterior Delta | QMPB | Posterior Beta |
| CEAT | Anterior Theta | AADL | Asymmetry Intrahemispheric Delta - Left |
| CEPT | Posterior Theta | AADR | Delta - Right |
| CEAA | Anterior Alpha | AATL | Theta - Left |
| CEPA | Posterior Alpha | AATR | Theta - Right |
| CEAB | Anterior Beta | AAAL | Alpha - Left |
| CEPB | Posterior Beta | AAAR | Alpha - Right |
| AEMD | Asymmetry interhemispheric Monopolar Delta | AABL | Beta - Left |
| AEMT | Theta | AABR | Beta - Right |
| AEMA | Alpha | CEBD | Coherence interhemispheric Bipolar Delta |
| AEMB | Beta | CEBT | Theta |
| AEBD | Asymmetry interhemispheric Bipolar Delta | CEBA | Alpha |
| AEBT | Theta | CEBB | Beta |
| AEBA | Alpha | RBDL | Relative power Bipolar Delta Left |
| AEBB | Beta | RBDR | Delta - Right |
| CADL | Coherence intrahemispheric Delta - Left | RBTL | Theta - Left |
| CADR | Delta - Right | RBTR | Theta - Right |
| CATL | Theta - Left | RBAL | Alpha - Left |
| CATR | Theta - Right | RBAR | Alpha - Right |
| CAAL | Alpha - Left | RBBL | Beta - Left |
| CAAR | Alpha - Right | RBBR | Beta - Right |

CHART 1.2

Electrode Composition of Multivariables

| Multivariable | Electrodes | | | | | | | | | | |
|---|---|---|---|---|---|---|---|---|---|---|---|
| RMAD | Fp1 | Fpz | Fp2 | F3 | FZ | F4 | F7 | F8 | C3 | Cz | C4 |
| RMPD | T3 | T4 | T5 | T6 | P3 | Pz | P4 | O1 | Oz | O2 | |
| RMAT | Fp1 | Fpz | Fp2 | F3 | FZ | F4 | F7 | F8 | C3 | Cz | C4 |

CHART 1.2-continued

Electrode Composition of Multivariables

| Multivariable | Electrodes | | | | | | | | | | |
|---|---|---|---|---|---|---|---|---|---|---|---|
| RMPT | T3 | T4 | T5 | T6 | P3 | Pz | P4 | O1 | Oz | O2 | |
| RMAA | Fp1 | Fpz | Fp2 | F3 | FZ | F4 | F7 | F8 | C3 | Cz | C4 |
| RMPA | T3 | T4 | T5 | T6 | P3 | Pz | P4 | O1 | Oz | O2 | |
| RMAB | Fp1 | Fpz | Fp2 | F3 | FZ | F4 | F7 | F8 | C3 | Cz | C4 |
| RMPB | T3 | T4 | T5 | T6 | P3 | Pz | P4 | O1 | Oz | O2 | |
| CEAD | FP1/FP2 | F3/F4 | F7/F8 | C3/C4 | | | | | | | |
| CEPD | T3/T4 | T5/T6 | P3/P4 | O1/O2 | | | | | | | |
| CEAT | FP1/FP2 | F3/F4 | F7/F8 | C3/C4 | | | | | | | |
| CEPT | T3/T4 | T5/T6 | P3/P4 | O1/O2 | | | | | | | |
| CEAA | FP1/FP2 | F3/F4 | F7/F8 | C3/C4 | | | | | | | |
| CEPA | T3/T4 | T5/T6 | P3/P4 | O1/O2 | | | | | | | |
| CEAB | FP1/FP2 | F3/F4 | F7/F8 | C3/C4 | | | | | | | |
| CEPB | T3/T4 | T5/T6 | P3/P4 | O1/O2 | | | | | | | |
| QMAD | Fp1 | Fpz | Fp2 | F3 | FZ | F4 | F7 | F8 | C3 | Cz | C4 |
| QMPD | T3 | T4 | T5 | T6 | P3 | Pz | P4 | O1 | Oz | O2 | |
| QMAT | Fp1 | Fpz | Fp2 | F3 | FZ | F4 | F7 | F8 | C3 | Cz | C4 |
| QMPT | T3 | T4 | T5 | T6 | P3 | Pz | P4 | O1 | Oz | O2 | |
| QMAA | Fp1 | Fpz | Fp2 | F3 | FZ | F4 | F7 | F8 | C3 | Cz | C4 |
| QMPA | T3 | T4 | T5 | T6 | P3 | Pz | P4 | O1 | Oz | O2 | |
| QMAB | Fp1 | Fpz | Fp2 | F3 | FZ | F4 | F7 | F8 | C3 | Cz | C4 |
| QMPB | T3 | T4 | T5 | T6 | P3 | Pz | P4 | O1 | Oz | O2 | |
| AEMD | FP1/FP2 | F3/F4 | F7/F8 | C3/C4 | T3/T4 | T5/T6 | P3/P4 | O1/O2 | | | |
| AEMT | FP1/FP2 | F3/F4 | F7/F8 | C3/C4 | T3/T4 | T5/T6 | P3/P4 | O1/O2 | | | |
| AEMA | FP1/FP2 | F3/F4 | F7/F8 | C3/C4 | T3/T4 | T5/T6 | P3/P4 | O1/O2 | | | |
| AEMB | FP1/FP2 | F3/F4 | F7/F8 | C3/C4 | T3/T4 | T5/T6 | P3/P4 | O1/O2 | | | |
| AADL | FP1/FP2 | F3/F4 | F7/F8 | C3/C4 | | | | | | | |
| AADR | T3/T4 | T5/T6 | P3/P4 | O1/O2 | | | | | | | |
| AATL | FP1/FP2 | F3/F4 | F7/F8 | C3/C4 | | | | | | | |
| AATR | T3/T4 | T5/T6 | P3/P4 | O1/O2 | | | | | | | |
| AAAL | FP1/FP2 | F3/F4 | F7/F8 | C3/C4 | | | | | | | |
| AAAR | T3/T4 | T5/T6 | P3/P4 | O1/O2 | | | | | | | |
| AABL | FP1/FP2 | F3/F4 | F7/FS | C3/C4 | | | | | | | |
| AABR | T3/T4 | T5/T6 | P3/P4 | O1/O2 | | | | | | | |
| CADL | FP1/FP2 | F3/F4 | F7/F8 | C3/C4 | | | | | | | |
| CADR | T3/T4 | T5/T6 | P3/P4 | O1/O2 | | | | | | | |
| CATL | FP1/FP2 | F3/F4 | F7/F8 | C3/C4 | | | | | | | |
| CATR | T3/T4 | T5/T6 | P3/P4 | O1/O2 | | | | | | | |
| CAAL | FP1/FP2 | F3/F4 | F7/F8 | C3/C4 | | | | | | | |
| CAAR | T3/T4 | T5/T6 | P3/P4 | O1/O2 | | | | | | | |
| CABL | FP1/FP2 | F3/F4 | F7/F8 | C3/C4 | | | | | | | |
| CABR | T3/T4 | T5/T6 | P3/P4 | O1/O2 | | | | | | | |
| RBDL | FP1/FP2 | F3/F4 | F7/F8 | C3/C4 | | | | | | | |
| RBDR | T3/T4 | T5/T6 | P3/P4 | O1/O2 | | | | | | | |
| RBTL | FP1/FP2 | F3/F4 | F7/F8 | C3/C4 | | | | | | | |
| RBTR | T3/T4 | T5/T6 | P3/P4 | O1/O2 | | | | | | | |
| RBAL | FP1/FP2 | F3/F4 | F7/F8 | C3/C4 | | | | | | | |
| RBAR | T3/T4 | T5/T6 | P3/P4 | O1/O2 | | | | | | | |
| RBBL | FP1/FP2 | F3/F4 | F7/F8 | C3/C4 | | | | | | | |
| RBBR | T3/T4 | T5/T6 | P3/P4 | O1/O2 | | | | | | | |
| AEBD | C3Cz/C4Cz | T3T5/T4T6 | P3O1/P4O2 | F7T3/F8T4 | | | | | | | |
| AEBT | C3Cz/C4Cz | T3T5/T4T6 | P3O1/P4O2 | F7T3/F8T4 | | | | | | | |
| AEBA | C3Cz/C4Cz | T3T5/T4T6 | P3O1/P4O2 | F7T3/F8T4 | | | | | | | |
| AEBB | C3Cz/C4Cz | T3T5/T4T6 | P3O1/P4O2 | F7T3/F8T4 | | | | | | | |
| CEBD | C3Cz/C4Cz | T3T5/T4T6 | P3O1/P4O2 | F7T3/F8T4 | | | | | | | |
| CEBT | C3Cz/C4Cz | T3T5/T4T6 | P3O1/P4O2 | F7T3/F8T4 | | | | | | | |
| CEBA | C3Cz/C4Cz | T3T5/T4T6 | P3O1/P4O2 | F7T3/F8T4 | | | | | | | |
| CEBB | C3Cz/C4Cz | T3T5/T4T6 | P3O1/P4O2 | F7T3/F8T4 | | | | | | | |

The variables in Chart 1.1 are represented by four letter abbreviations. The first two or three letters of the abbreviations are primary designators. The primary designators RB, RM, CA, CE, QM, AA, and AE indicate what type of QEEG measurement is referenced. For example, the primary designator "RM" is relative monopolar power. "RB" is relative bipolar power. "CA" is intrahemispheric coherence. "CEB" is interhemispheric bipolar coherence. "QM" is monopolar frequency. "AA" is intrahemispheric asymmetry. "AE" is interhemispheric asymmetry.

The one or last two letters of the multivariable abbreviations are secondary designators. The secondary designators indicate the groups of electrodes and frequency bands from which the measurements are drawn. Measurements are drawn from electrodes in the anterior or ("A"), posterior ("P") regions of the scalp, the left ("L") or right ("R") sides of the scalp. Measurements are made in the delta ("D"), theta ("T"), alpha ("A"), or beta ("B") frequency bands.

According to Chart 1.1, "RMAD" (relative power monopolar anterior delta) is the relative monopolar power in the delta frequency measured at the electrodes located on the front half of the scalp. Similarly, "RBDL" is the relative bipolar power measured by the electrodes in the left half of the scalp for the delta frequency band. "CABL" is intrahemispheric coherence measured from the electrodes in the left region of the scalp in the beta frequency band. "CADR" is the intrahemispheric coherence measured at the electrodes in the right region of the scalp for the delta frequency band. "AED" is monopolar asymmetry measured interhemispherically in the delta frequency band.

IC. Calculating Z Values for Multivariables

As indicated previously, preliminary to the method of the present invention, Z values are determined for each of the univariate variables in the neurometric information set by either Spectrum 32 or NxLink software. According to the invention, these univariate variables are then aggregated into the composite multivariate clinical descriptors, according to the description provided in Chart 1.1, using special weighting functions for the electrodes of interest.

The weighting functions are mathematical transforms that are empirically derived from patient data. Using the weighting functions allows for the scaling of multivariables that are derived from measurements from different numbers of electrodes or pairs of electrodes, called components. Table 1 summarizes the mathematical weighting functions of the present invention.

TABLE 1

Multivariable Weighting Functions and Transforms

| Name | Description | Transform & Weighting Function |
|---|---|---|
| $RMAX^a$ | Relative power Monopolar Anterior | $12/10 \sum_{10}^{1} RMA?\ldots RMA?n$ |
| $RMPX^a$ | Relative power Monopolar Posterior | $12/11 \sum_{10}^{1} RMP?1\ldots RMP?n$ |
| $QMAX^a$ | Frequency Monopolar Anterior | $12/10 \sum_{10}^{1} QMA?1\ldots QMA?n$ |
| $QMPX^a$ | Frequency Monopolar Posterior | $12/11 \sum_{11}^{1} QMP?1\ldots QMP?n$ |

TABLE 1-continued

Multivariable Weighting Functions and Transforms

| Name | Description | Transform & Weighting Function |
|---|---|---|
| $CEAX^a$ | Coherence interhemispheric Anterior | $\sqrt[3.6]{\sum_{n}^{1} CEA?1^3 \ldots CEA?n^3}$ |
| $AEMX^a$ | Asymmetry interhemispheric Monopolar | $\sqrt[3.6]{\sum_{n}^{1} AEM?1^3 \ldots AEM?n^3}$ |
| $AEBX^a$ | Asymmetry interhemispheric Bipolar | $\sqrt[3.6]{\sum_{n}^{1} AEB?1^3 \ldots AEB?n^3}$ |
| $AAYX^a$ | Asymmetry intrahemispheric | $\sqrt[3.6]{\sum_{n}^{1} AA??1^3 \ldots AA??n^3}$ |
| $CEBX^a$ | Coherence interhemispheric | $\sqrt[3.6]{\sum_{n}^{1} CEB?1^3 \ldots CEB?n^3}$ |
| $RBYX^a$ | Relative power Bipolar | $\sqrt[3.6]{\sum_{n}^{1} RB??1^3 \ldots RB??n^3}$ |
| $CAYX^a$ | Coherence intrahemispheric | $\sqrt[3.6]{\sum_{n}^{1} CA??1^3 \ldots CA??n^3}$ |

$^a$ X = D, T, A, B;
$^a$ X = D, T, A, B; Y = L, R

Using the weighting functions summarized in Table 1, patient specific neurophysiologic data is obtained. The following embodiment illustrates the process for the determination of the magnitude of a particular multivariable for an individual patient. The value of the multivariable CEAD [Coherence interhemispheric Anterior Delta] for a patient is given in its algorithmic form in Table 2.

TABLE 2

Sample Calculation of Clinical Multivariate CEAD Measure

| | Component 1 | Component 2 | Component 3 | Component 4 |
|---|---|---|---|---|
| Electrode pair | Fp1/Fp2 | F3/F4 | F7/F8 | C3/C4 |
| Univariate Z Score | −0.982 | −1.036 | −1.230 | −0.249 |
| Weighting Function, $C^3$ | −0.947 | −1.112 | −1.861 | −0.015 |
| Collect Terms | | | | |
| Fp1/Fp2 + F3/F4 | | −2.059 | | |
| F7/F8 + C3/C4 | | | | −1.876 |
| Square Collected Terms | | 4.239 | | 3.520 |
| Sum of Squares | 7.760 | | | |
| Sign Correction$^a$ | −1 | | | |
| CEAD | −8 | | | |

$^a$ negative if sum of terms is negative

Table 2 indicates that the CEAD multivariable is calculated from readings collected at four electrode pairs, designated by their names under the International 10/20 system. The electrode pairs are referred to as components 1-4. Z scores are calculated for each electrode pair. The Z scores are normalized using a weighting function, $C^3$, as indicated in Table 1. The process of normalization makes it possible to mathematically combine the Z scores. The square is calculated for the sum of each of the components of CEAD. The values are then mapped into a "clinical decision" interval ranging from −40 to +40. This mapping creates an integer scale of uniform change for each of the multivariable descriptors. Thus, the weighted Z scores calculated for the electrode pairs within the same brain hemisphere were summed (Fp1/Fp2+F3/F4=−2.059; F7/F8+C3/C4=−1.876), squared, ($-2.059^2$=4.239; $-1.876^2$=3.520), and added together (4.239+3.520=7.760). The sign of the final product was corrected and rounded off to the nearest whole number (−7.760→−8).

Generalizing the process of multivariate classification in an incremental fashion from the example above creates a table of similarly derived measures for an individual patient. A medication-response-specific characterization of brain dysfunction for an individual patient is summarized according to each multivariable in Table 3.

TABLE 3.1

Multivariables for an Individual Patient

| Multivariable | Value | Multivariable | Value |
|---|---|---|---|
| RMAD | −35 | CABL | 5 |
| RMPD | −23 | CABR | 10 |
| RMAT | −40 | FMAD | −34 |
| RMPT | −33 | FMPD | −30 |
| RMAA | 40 | FMAT | 3 |
| RMPA | 27 | FMPT | 5 |
| RMAB | −30 | FMAA | 33 |
| RMPB | −21 | FMPA | 15 |
| CEAD | 4 | FMAB | −4 |
| CEPD | 0 | FMPB | 10 |
| CEAT | 5 | AADL | 0 |
| CEPT | 5 | AADR | 1 |
| CEAA | −1 | AATL | 3 |
| CEPA | 40 | AATR | 3 |
| CEAB | 10 | AAAL | 3 |
| CEPB | 20 | AAAR | 3 |
| AEMD | −6 | AABL | 0 |
| AEMT | −6 | AABR | 0 |
| AEMA | 9 | CEBD | 2 |
| AEMB | −9 | CEBT | 2 |
| AEBD | −1 | CEBA | 26 |
| AEBT | −1 | CEBB | 3 |
| AEBA | −5 | RBDL | −13 |
| AEBB | −1 | RBDR | −10 |
| CADL | 2 | RBTL | −18 |
| CADR | 1 | RBTR | −21 |
| CATL | 1 | RBAL | 21 |
| CATR | 1 | RBAR | 22 |
| CAAL | 18 | RBBL | −12 |
| CAAR | 11 | RBBR | −11 |

In the example summarized in Table 3, the patient has a RMAA value of 40. This value would be expected to occur in the normal population only 3 times in 100,000 observations. A patient with this RMAA value would be judged as having a physiologic brain imbalance of the RMAA type and would be classified accordingly. The information summarized in Tables 1-3 and the related charts and drawings characterize an individual patient's physiologic brain imbalance as detected by EEGQEEG and compared to database information collected from individual persons clinically determined to be asymptomatic.

II. Characterizing and Treating Physiologic Brain Imbalances with Neurometric Information In another aspect, the EEG/QEEG analysis of the present invention is designed to identify therapy regimes for changing, or "correcting," from the "abnormal" or symptomatic state to the "normal" or "asymptomatic" state the physiologic brain imbalances detected by EEG/QEEG. These treatment modalities include, but are not limited to drug therapy, electroconvulsive therapy, electromagnetic therapy, neuromodulation therapy, verbal therapy, and other forms of therapy known to, or currently under development in the art. The present invention is thus also directed to a method for making recommendations for the treatment of physiologic brain imbalances using neurophysiologic information such as EEG/QEEG, as depicted in FIGS. 1 and 2.

According to FIG. 2, steps c and $c_1$, EEG-based treatment recommendations are not proposed for a patient with a "normal" EEG/QEEG. EEG/QEEG findings for a patient that are found to be "indeterminate" are repeated at a later time (e.g., step d). Treatment recommendations are made for patients with "abnormal EEG/QEEGs (e.g., steps e-f). Treatment recommendations can involve "monotherapy," or single agent therapy (step $f_1$) or multiple agent therapy (step $f_2$).

IIA. Treating Physiologic Brain Imbalances

The characterizing and treating steps of the method of the present invention uses an "Outcomes Database" to guide assessment, as well as treatment selection and implementation, for individuals with physiologic brain imbalances. In one aspect, a "psychiatric" Outcomes Database is constructed using EEG/QEEG information from individuals who are behaviorally diagnosed with a range of imbalances and who are undergoing or who have undergone drug therapy for behavioral pathologies (e.g., FIG. 1, step k). The disorders contained in the database include, but are not limited to the following: agitation, attention deficit hyperactivity disorder, abuse, Alzheimer's disease/dementia, anxiety, panic, and phobic disorders, bipolar disorders, borderline personality disorder, behavior control problems, body dysmorphic disorder, cognitive problems, depression, dissociative disorders, eating, appetite, and weight problems, edema, fatigue, hiccups, impulse-control problems, irritability, mood problems, movement problems, obsessive-compulsive disorder, pain, personality disorders, posttraumatic stress disorder, schizophrenia and other psychotic disorders, seasonal affective disorder, sexual disorders, sleep disorders, stuttering, substance abuse, tic disorders/Tourette's Syndrome, traumatic brain injury, Trichotillomania, or violent/self-destructive behaviors.

In this aspect of the invention, the EEG/QEEG method can be used to guide choices for treating the above-listed psychiatric disorders with various therapeutic regimes, including, but not limited to: drug therapy, electroconvulsive therapy, electromagnetic therapy, neuromodulation therapy, verbal therapy, and other forms of therapy described by the psychiatric and neurologic art.

Drug therapy guided by these physiological features is possible with minimal modification of the clinicians' current practices. In one aspect of the invention, a patient's multivariable Z scores are compared directly with the information contained in the "symptomatic" database. However, it is preferable to perform the treatment in two steps. That is, the patient's pretreatment multivariable EEG/QEEG information is obtained and compared firstly with EEG/QEEG information contained in the "asymptomatic" database, and secondly with information contained in the "symptomatic" database. The "symptomatic" database contains information for patients with known medication responsivity profiles (e.g., FIG. 1, step k). Next, the robustness of the statistical association of the current patient's EEG/QEEG information with the database of previously treated individuals is determined. The degree of statistical robustness can provide a physiological basis for the selection of medication.

In the drug therapy aspect of the present invention, EEG/QEEG information from a patient, who has a physiologic brain imbalance, is compared to multivariate outcome measures in the Outcomes Database. By comparing the patient EEG/QEEG information to the Outcomes Database EEG/QEEG multivariate measurements, it is possible to identify drug treatments that are likely to correct EEG/QEEG abnormalities. For example, the patient, whose information was previously presented, with an RMAA of 40 (cf, Table 3), belongs to a group of individuals who have responded positively to the antidepressant class of drugs, or more particularly to a group of agents which normalize RMAA. A clinician can use this measure to guide therapeutic choices.

At least two types of analysis are possible according to the method of the present invention—Type One and Type Two Analysis. Type One Analysis provides that patients are drug and medication free. Type Two Analysis, discussed below, provides for patients who will not or cannot be medication free. Medication status must preferably duplicate that of the referential control population as well as fulfill the definition of a baseline measurement (less than 1 percent residual medication). Patients are preferably free of medication for at least seven half-lives of their prior medication and its metabolites. The Type One patient's baseline EEG/QEEG is then matched with similar EEG/QEEG's and their correlated medication outcomes in the Outcomes Database. As indicated, the Outcomes Database is the "symptomatic" database containing the multivariate Z scores of patients with psychiatric and/or neurologic imbalances and the treatment modalities that convert the abnormal multivariate Z scores of these patients to normal. Next, a neuroactive medication candidate is identified in the Outcomes Database according to its physiological effects on brain function. Each medication is classified by its influence on EEG/QEEG information. This procedure furnishes the physician with a physiological link between the agents and their effect on brain function across diverse symptomatic behavioral expressions.

The probability that a patient will respond to different types of pharmacologic agents is then determined. These pharmacologic agents, classes of agents, or combination of agents or classes of agents include antidepressants, antianxiety agents, side effect control agents, treatments for alcohol abuse, mood stabilizers, anti-ADD agents, antipsychotics and hypnotic agents.

The procedure for determining the response probability classifies the untreated patient into one of the diverse subtypes of medication response profile that occur within and across DSM imbalances. The procedure compares the patient's Z score profile with the Outcomes Database described above. The Outcomes Database of the present method is designed to track responsivity profiles based on EEG/QEEG information for a number of drugs, known by their generic names such as, for example: alprazolam, amantadine, amitriptyline, atenolol, bethanechol, bupropion, buspirone, carbamazepine, chlorpromazine, chlordiazepoxide, citalopram, clomipramine, clonidine, clonazepam, clozapine, cyproheptadine, divalproex, deprenyl, desipramine, dextroamphetamine, diazepam, disulfiram, divalproex, doxepin, ethchlorvynol, fluoxetine, fluvoxamine, felbamate, fluphenazine, gabapentin, haloperidol, imipramine, isocarboxazid, lamotrigine, levothyroxine, liothyronine, lithium carbonate, lithium citrate, lorazepam, loxapine, maprotiline, meprobamate, mesoridazine, methamphetamine, midazolam, meprobamate, mirtazepine, molindone, moclobemide, naltrexone, phenelzine, nefazodone, nortriptyline, olanzapine, oxazepam, paroxetine, pemoline, perphenazine, phenelzine, pimozide, pindolol, prazepam, propranolol, protriptyline, quetiapine, reboxetine, risperidone, selegiline, sertraline, sertindole, trifluoperazine, trimipramine, temazepam, thioridazine, topiramate, tranylcypromine, trazodone, triazolam, trihexyphenidyl, trimipramine, valproic acid or venlafaxine.

Responsivity profiles based on EEG/QEEG information is possible for medicinal agents having the following trademarks, for example, Adapin, Altruline, Antabuse, Anafranil, Aropax, Aroxat, Artane, Ativan, Aurorix, Aventyl, Buspar, Catapres, Celexa, Centrax, Cibalith-S, Cipramil, Clozaril, Cylert, Cytomel, Decadron, Depakene, Depakote, Deprax, Desoxyn, Desyrel, Dexedrine, Dextroamphetamine, Dobupal, Dormicum, Dutonin, Edronax, Elavil, Effexor, Eskalith, Eufor, Fevarin, Felbatol, Haldol, Helix, Inderal, Klonopin, Lamictal, Librium, Lithonate, Lithotabs, Loxitane, Ludiomil, Lustral, Luvox, Manerex, Marplan, Miltown, Moban, Nalorex, Nardil, Nefadar, Neurontin, Norpramin, Nortrilen, Orap, Pamelor, Parnate, Paxil, Periactin, Placidyl, Prisdal, Prolixin, Prozac, Psiquial, Ravotril, Remeron, ReVia, Risperdal, Ritalin, Saroten, Sarotex, Serax, Sercerin, Serlect, Seroquel, Seropram, Seroxat, Serzone, Symmetrel, Stelazine, Surmontil, Synthroid, Tegretol, Tenormin, Thorazine, Tofranil, Tolrest, Topamax, Tranxene, Trilafon, Typtanol, Tryptizol, Urecholine, Valium, Verotina, Vestal, Vivactil, Wellbutrin, Xanax, Zoloft, or Zyprexa. The generic descriptions of these trademarked agents and their source are available from the Physicians Desk Reference (New York: Medical Economics Company, 2000), the descriptions of which are herein incorporated by reference.

Because the EEG/QEEG information of the present invention link medications to their effects on brain function, a new pharmaceutical nomenclature in which agents are identified by their electrotherapeutic profile is appropriate. Table 4 contains selected drug agents in the database of the present invention, electrotherapeutically classified by 72 discriminating features.

According to Table 4.1, a drug response prediction can be made based on the magnitude of observed EEG/QEEG parameters. For example, an absolute power average greater than 300 microvolts squared (e.g., QEEG Parameter 1) predicts a response to the antidepressant class or alpha-2 agonist class of drugs; or in the nomenclature of the present invention, to drugs in electrotherapeutic classes 1.11-1.23. As Table 4.1 suggests, a particular QEEG parameter reading may predict a response to single or multiple drug classes. To that end, a ratio of frontal to posterior alpha indices less than 4 (e.g., QEEG Parameter 1) predicts a response to multiple electrotherapeutic drug classes. Similar results are reflected in Tables 4.2-4.6. Table 4.7 lists in alphabetical order the names of the drugs or drug classes appearing in Tables 4.1-4.6

TABLE 4.1

| QEEG PARAMETERS & INDICES 1-12 | | | | | | |
|---|---|---|---|---|---|---|
| | 1 | 2 | 3 | 4 | 5 | 6 |
| QEEG PARAMETERS & INDICES 1-12 | QEEG ABSOLUTE POWER AVERAGE = >300 MICROVOLTS SQUARED | QEEG ABSOLUTE POWER AVERAGE = <300 & >50 MICROVOLTS SQ. | QEEG ABSOLUTE POWER AVERAGE = <50 MICROVOLTS SQUARED | FRONTAL MIDLINE PROGRESSION INDEX (ALPHA BAND) = >2.5 | FRONTAL MIDLINE PROGRESSION ION INDEX (ALPHA BAND) = <2.5 | POSTERIOR MIDLINE PROGRESSION INDEX (ALPHA BAND) = >1 |
| PREDICTS RESPONSE TO 1.11-2.3 AGENTS: (ANTIDEPRESS-ANTS/ALPHA-2 AGONIST) | SSRI SNRI TCA CLONIDINE | SSRI SNRI TCA BUPROPRN MAOI CLONIDINE | BUPROPRION MAOI | SSRI SNRI TCA (1.11-1.23) | SSRI SNRI TCA (1.22-1.31) | SSRI SNRI TCA (1.11-1.31) |
| PPREDICTS RESPONSE TO 2.4-2.8 AGENTS (STIMULANTS) | | STIMULANT | STIMULANT MAOI | | STIMU-LANT | |
| PPREDICTS RESPONSE TO 3.0-3.9 AGENTS: LITHIUM/ANTI-CONVULSANTS/ BENZO-DIAZEPINES/BETA BLOCKERS* | | | VALPROATE BENZODIAZ BETA BLKR | | | |

| | 7 | 8 | 9 | 10 | 11 | 12 |
|---|---|---|---|---|---|---|
| QEEG PARAMETERS & INDICES 1-12 | POSTERIOR MIDLINE PROGRESSION INDEX (ALPHA BAND) = <1 | RATIO OF FRONTAL/ POSTERIOR ALPHA INDICES = >4 | RATIO OF FRONTAL/ POSTERIOR ALPHA INDICES = <4 | AVERAGE MIDLINE (FPZ, FZ, CZ) THETA/ BETA RATIO = >2.5 | AVERAGE MIDLINE (FPZ, FZ, CZ) THETA/ BETA RATIO = <2.5 & >1.5 | AVERAGE MIDLINE (FPZ, FZ, CZ) THETA/ BETA RATIO = <1.5 |
| PREDICTS RESPONSE TO 1.11-2.3 AGENTS: (ANTIDEPRESS-ANTS/ALPHA-2 AGONIST) | BUPROPRION, MAOI +/− STIMULANT | SSRI SNRI TCA (1.11-1.3) | SNRI BUPROPRION MAOI | SNRI TCA (1.31) BUPROPRION MAOI | SNRI SSRI TCA (1.31) BUPROPRION CLONIDINE | SSRI TCA (1.11-1.23) CLONIDINE |
| PPREDICTS RESPONSE TO 2.4-2.8 AGENTS (STIMULANTS) | STIMULANT +/− BUPROPRIO MAOI | | STIMULANT | STIMULANT MAOI | | |
| PPREDICTS RESPONSE TO 3.0-3.9 AGENTS: LITHIUM/ANTI-CONVULSANTS/ BENZO-DIAZEPINES/BETA BLOCKERS* | VALPROATE BENZODIAZ BETA BLKR | | VALPROATE BENZODIAZ BETA BLKR | VALPROATE BENZODIAZ BETA BLKR | CRBMAZPN | |

TABLE 4.2

| QEEG PARAMETERS & INDICES 13-24 | | | | | | |
|---|---|---|---|---|---|---|
| | 13 | 14 | 15 | 16 | 17 | 18 |
| QEEG PARAMETERS & INDICES 13-24 | MAD = >10 +/− RMPD = >10 | MAD = <10 +/− RMPD = <10 | MAT = >10 +/− RMPT = >10 | MAT = <10 +/− RMPT = <10 | MAA = >10 +/− RMPA = >10 | MAA = <10 +/− RMPA = <10 |
| PREDICTS RESPONSE TO 1.11-2.3 AGENTS: (ANTIDEPRESS-ANTS/ALPHA-2 AGONIST) | | SSRI SNRI TCA (1.22-1.31) CLONIDINE | BUPROPRN MAOI | SSRI SNRI TCA CLONIDINE | SSRI SNRI TCA (1.22-1.31) CLONI-DINE | MAOI |
| PREDICTS | STIMULANT | | STIMULANT | | | STIMULANT |

TABLE 4.2-continued

QEEG PARAMETERS & INDICES 13-24

| RESPONSE TO 2.4-2.8 AGENTS (STIMULANTS) | MAOI | | MAOI | | MAOI | |
|---|---|---|---|---|---|---|
| PREDICTS RESPONSE TO 3.0-3.9 AGENTS: LITHIUM/ ANTICONVUL- SANTS/ BENZODIAZE- PINES/BETA BLOCKERS* | | | VALPROATE BENZODIAZ | CRBMAZPN | CRBMZEPN | |

| | 19 | 20 | 21 | 22 | 23 | 24 |
|---|---|---|---|---|---|---|
| QEEG PARAMETERS & INDICES 13-24 | MAB = >10 +/− RMPB = >10 | MAB = <10 +/− RMPB = <10 | EAD = >10 +/− CEPD = >10 | EAD = <10 +/− CEPD = <10 | EAT = >10 +/− CEPT = >10 | EAT = <10 +/− CEPT = <10 |
| PREDICTS RESPONSE TO 1.11-2.3 AGENTS: (ANTIDEPRESS-ANTS/ALPHA-2 AGONIST) | SSRI SNRI TCA (1.11-1.21) | | | | | |
| PREDICTS RESPONSE TO 2.4-2.8 AGENTS (STIMULANTS) | | STIMULANT MAOI | | | | |
| PREDICTS RESPONSE TO 3.0-3.9 AGENTS: LITHIUM/ ANTICONVUL- SANTS/ BENZODIAZE- PINES/BETA BLOCKERS* | VALPROATE BETA BLKR | BENZODIAZ | VAL- PROATE BENZODIAZ | LITHIUM CRBMZEPN | VALPRO- ATE BENZODIAZ | LITHIUM CRBMZEPN |

TABLE 4.3

QEEG PARAMETERS & INDICES 25-36

| | 25 | 26 | 27 | 28 | 29 | 30 |
|---|---|---|---|---|---|---|
| QEEG PARAMETERS & INDICES 25-36 | CEAA = >10 +/− CEPA = >10 | CEAA = <10 +/− CEPA = <10 | CEAB = >10 +/− CEPB = >10 | CEAB = <10 +/− CEPB = <10 | FMAD = >10 +/− FMPD = >10 | FMAD = <10 +/− FMPD = <10 |
| PREDICTS RESPONSE TO 1.11-2.3 AGENTS: (ANTIDEPRESS-ANTS/ALPHA-2 AGONIST) | SSRI SNRI TCA | | SSRI SNRI TCA | | SSRI SNRI TCA (1.31) | SSRI SNRI TCA (1.1-1.23) |
| PREDICTS RESPONSE TO 2.4-2.8 AGENTS (STIMULANTS) | | | | | STIMULANT MAOI | |
| PREDICTS RESPONSE TO 3.0-3.9 AGENTS: LITHIUM/ ANTICONVUL- SANTS/ BENZODIAZE- PINES/BETA BLOCKERS* | LITHIUM CRBMZEPN BETA BLKR | | LITHIUM VALPROATE CRBMZEPN BETA BLKR | | BENZODIAZ | |

TABLE 4.3-continued

QEEG PARAMETERS & INDICES 25-36

| | 31 | 32 | 33 | 34 | 35 | 36 |
|---|---|---|---|---|---|---|
| QEEG PARAMETERS & INDICES 25-36 | FMAT = >10 +/− FMPT = >10 | FMAT = <10 +/− FMPT = <10 | FMAA = >10 +/− FMPA = >10 | FMAA = <10 +/− FMPA = <10 | FMAB = >10 +/− FMPB = >10 | FMAB = <10 +/− FMPB = <10 |
| PREDICTS RESPONSE TO 1.11-2.3 AGENTS: (ANTIDEPRESS-ANTS/ALPHA-2 AGONIST) | BUPRPRN SNRI TCA (1.31) CLONIDINE | SSRI TCA (1.11-1.23) CLONIDINE | SSRI TCA (1.1-1.23) CLONIDINE | BUPRPRN SNRI MAOI | SSRI: (1.41-1.43, 1.51) | SNRI SSRI: (1.41-1.43, 1.51) |
| PREDICTS RESPONSE TO 2.4-2.8 AGENTS (STIMULANTS) | STIMULANT MAOI | | | STIMULNAT MAOI | | STIMULANT MAOI |
| PREDICTS RESPONSE TO 3.0-3.9 AGENTS: LITHIUM/ ANTICONVUL-SANTS/ BENZODIAZE-PINES/BETA BLOCKERS* | BENZODIAZ | | BETA BLKR CRBMZEPN LITHIUM | BENZODIAZ VALPROATE | BETA BLKR CRBMZEPN LITHIUM | BENZODIAZ VALPROATE |

TABLE 4.4

QEEG PARAMETERS & INDICES 37-48

| | 37 | 38 | 39 | 40 | 41 | 42 |
|---|---|---|---|---|---|---|
| QEEG PARAMETERS & INDICES 37-48 | AADL = >10, OR AADR = >10 | AADL = <10, OR AADR = <10 | AATL = >10, OR AATR = >10 | AATL = <10, OR AATR = <10 | AAAL = >10, OR AAAR = >10 | AAAL = <10, OR AAAR = <10 |
| PREDICTS RESPONSE TO 1.11-2.3 AGENTS: (ANTIDEPRESSANTS/ ALPHA-2 AGONIST) | | SSRI SNRI TCA (1.22-1.31) | | SSRI SNRI TCA (1.22-1.31) | SSRI SNRI TCA (1.22-1.31) | |
| PREDICTS RESPONSE TO 2.4-2.8 AGENTS (STIMULANTS) | STIMULANT MAOI | STIMULANT MAOI | STIMULANT MAOI | | | STIMU-LANT MAOI |
| PREDICTS RESPONSE TO 3.0-3.9 AGENTS: LITHIUM/ ANTICONVUL-SANTS/ BENZODIAZE-PINES/BETA BLOCKERS* | | | | | | |

| | 43 | 44 | 45 | 46 | 47 | 48 |
|---|---|---|---|---|---|---|
| QEEG PARAMETERS & INDICES 37-48 | AABL = >10, OR AABR = >10 | AABL = <10, OR AABR = <10 | AED = >10, AND/OR AET = >10 | AET = <10, AND/OR AET = <10 | AEA = >10, AND/OR AEA = <10 | AEB = >10, AND/OR AEB = <10 |
| PREDICTS RESPONSE TO 1.11-2.3 AGENTS: (ANTIDEPRES-SANTS/ALPHA-2 AGONIST) | | SSRI SNRI TCA (1.11-1.21) | | | | |
| PREDICTS RESPONSE TO 2.4-2.8 AGENTS (STIMULANTS) | | | | | | |

TABLE 4.4-continued

| QEEG PARAMETERS & INDICES 37-48 | | | | |
|---|---|---|---|---|
| PREDICTS RESPONSE TO 3.0-3.9 AGENTS: LITHIUM/ ANTICONVUL- SANTS/ BENZODIAZE- PINES/BETA BLOCKERS* | LITHIUM/ ANTI- CONVULSANT/ BENZO (3.X AGENT) | LITHIUM/ ANTI- CONVULSANT/ BENZO (3.X AGENT) | LITHIUM/ ANTI- CONVULSANT/ BENZO (3.X AGENT) | LITHIUM/ ANTI- CONVULSANT/ BENZO (3.X AGENT) |

TABLE 4.5

| QEEG PARAMETERS & INDICES 49-60 | | | | | | |
|---|---|---|---|---|---|---|
| | 49 | 50 | 51 | 52 | 53 | 54 |
| QEEG PARAMETERS & INDICES 49-60 | AEBD = >10 AND/OR AEBD = <10 | AEBT = >10 AND/OR AEBT = <10 | AEBA = >10 AND/OR AEBA = <10 | AEBB = >10 AND/OR AEBB = <10 | CADL = >10, OR = <10 | CADR = >10, OR = <10 |
| PREDICTS RESPONSE TO 1.11-2.3 AGENTS: (ANTI- DEPRESSANTS/ ALPHA-2 AGONIST) | | | | | | |
| PREDICTS RESPONSE TO 2.4-2.8 AGENTS (STIMULANTS) | | | | | | |
| PREDICTS RESPONSE TO 3.0-3.9 AGENTS: LITHIUM/ ANTI- CONVULSANTS/ BENZODIAZEPINES/ BETA BLOCKERS* | LITHIUM/ ANTI- CONVULSANT/ BENZO (3.X AGENT) | LITHIUM/ ANTI- CONVULSANT/ BENZO (3.X AGENT) | LITHIUM/ ANTI- CONVULSANT/ BENZO (3.X AGENT) | LITHIUM/ ANTI- CONVULSANT/ BENZO (3.X AGENT) | VALPROATE BENZODIAZ | VALPROATE BENZODIAZ |

| | 55 | 56 | 57 | 58 | 59 | 60 |
|---|---|---|---|---|---|---|
| QEEG PARAMETERS & INDICES 49-60 | CATL = >10, OR = <10 | CATR = >10, OR = <10 | CAAL = >10, OR = <10 | CAAR = >10, OR = <10 | CABL = >10, OR = <10 | CABR = >10, OR = <10 |
| PREDICTS RESPONSE TO 1.11-2.3 AGENTS: (ANTI- DEPRESSANTS/ ALPHA-2 AGONIST) | | | | | | |
| PREDICTS RESPONSE TO 2.4-2.8 AGENTS (STIMULANTS) | | | | | | |
| PREDICTS RESPONSE TO 3.0-3.9 AGENTS: LITHIUM/ ANTI- CONVULSANTS/ BENZODIAZEPINES/ BETA BLOCKERS* | VALPROATE BENZODIAZ | VALPROATE BENZODIAZ | CRBMZEPN BETA BLKR | CRBMZEPN BETA BLKR | VALPROATE BETA BLKR | VALPROATE BETA BLKR |

TABLE 4.6

QEEG PARAMETERS & INDICES 61-72

| | 61 | 62 | 63 | 64 | 65 | 66 |
|---|---|---|---|---|---|---|
| QEEG PARAMETERS & INDICES 61-72 | CEBD = >10, OR = <10 | CEBT = >10, OR = <10 | CEBA = >10, OR = <10 | CEBB = >10, OR = <10 | RBDL = >10, AND/OR RBDR = >10 | RBDL = >10, AND/OR RBDR = <10 |
| PREDICTS RESPONSE TO 1.11-2.3 AGENTS: (ANTIDEPRESSANTS/ALPHA-2 AGONIST) | | | | | | SSRI SNRI TCA (1.22-1.31) CLONIDINE |
| PREDICTS RESPONSE TO 2.4-2.8 AGENTS (STIMULANTS) | | | | | STIMULANT MAOI | STIMULANT MAOI |
| PREDICTS RESPONSE TO 3.0-3.9 AGENTS: LITHIUM/ ANTICONVULSANTS/ BENZODIAZEPINES/BETA BLOCKERS* | VALPROATE BENZODIAZ | VALPROATE BENZODIAZ | CRBMZEPN BETA BLKR | CRBMZEPN VALPROATE BETA BLKR | | |

| | 67 | 68 | 69 | 70 | 71 | 72 |
|---|---|---|---|---|---|---|
| QEEG PARAMETERS & INDICES 61-72 | RBTL = >10, AND/OR RBTR = >10 | RBTL = <10, AND/OR RBTR = <10 | RBAL = >10, AND/OR RBAR = >10 | RBAL = <10, AND/OR RBAR = <10 | RBBL = >10, AND/OR RBBR = >10 | RBBL = <10, AND/OR RBBR = <10 |
| PREDICTS RESPONSE TO 1.11-2.3 AGENTS: (ANTIDEPRESSANTS/ALPHA-2 AGONIST) | | SSRI SNRI TCA (1.11-1.31) CLONIDINE | SSRI SNRI TCA (1.22-1.31) CLONIDINE | | SSRI SNRI TCA (1.11-1.31) CLONIDINE | |
| PREDICTS RESPONSE TO 2.4-2.8 AGENTS (STIMULANTS) | BPROPRN STIMULANT MAOI | | | | STIMULANT MAOI | |
| PREDICTS RESPONSE TO 3.0-3.9 AGENTS: LITHIUM/ ANTICONVULSANTS/ BENZODIAZEPINES/BETA BLOCKERS* | | | | | LITHIUM | |

TABLE 4.7

Abbreviation Key for Tables 4.1–4.6

| Abbreviation | Name |
|---|---|
| Benzo | Benzodiazepine |
| Benzodiaz | Benzodiazepine |
| Beta Blkr | Beta Blocker |
| Buproprn | Buprorion |
| CRBMAZPN | Carbamazepine |
| MAOI | Monoamine Oxidase Inhibitor |
| SSRI | Selective Serotonin Reuptake Inhibitor |
| SNRI | Seretonin Norepinephrine Reuptake Inhibitor |
| TCA | Tricyclic Antidepressant |

According to the Type Two Analysis procedure, individuals who cannot be tested according to Type One Analysis can be tested under conditions where ongoing medications are allowed. Type Two Analysis reports the impact of medication on the EEG/QEEG information. Follow-up EEG recordings are used to track changes produced by the administration of medications. When Type Two Analysis has been preceded by Type One Analysis, it is possible to observe the absolute changes attributable to medication and appreciate the spectrum of actions on the EEG/QEEG of a given medication or combination of medications. These effects can be compared to the set of initially comparable individuals and their response to the same medication or medications. When the information for the current patient and the reference group within the Outcomes Database are substantially similar, this comparison further validates the characteristics of the medication and helps to refine the electrotherapeutic class of the medication. In the absence of such confirmation the patient's information are not allowed into the Outcomes Database. This provides a quantitative quality assurance standard and segregates those individuals requiring further study.

For patients analyzed according to Type Two Analysis without a preceding Type One Analysis, therapeutic guidance is derived from treating the information as if it were derived from Type One Analysis and adjusting medication using both the electrotherapeutic agent recommendation and the current medication information. After the steady state has been reach for the new medications, a follow-up Type Two Analysis can be treated in a manner similar to the patient who had an initial Type One Analysis. No one can be added to the Outcomes Database without an initial Type One Analysis.

In follow-up studies, the patient is examined by the treating physician and receives a Clinical Global Improvement (CGI) score. The CGI score is used to gauge the behavioral success of a given therapy regime for improving or correcting the patients disturbance. Typically a treating physician will assign a CGI score of −1 to 3 to a patient based on observed behavioral indicia. In the context of the drug therapy embodiment, a CGI score of negative one (−1) indicates an adverse medication effect. A CGI score of zero (0) indicates no improvement. A CGI score of one (1) indicates minimal or mild improvement. A CGI score of two 2 indicates moderate improvement. Finally, a CGI score of three (3) indicates marked improvement, including complete absence of symptoms.

The EEG Report Use Algorithm and associated flow charts (cf. FIGS. 3-7) summarize several embodiments or examples of the clinical procedure developed according to the treatment method of the present invention. These examples are useful for the optimization of treatment regimes for individual patients with physiologic brain imbalances. Although subject to revision as new agents and more information are added to the database, these algorithms offer a guide for improving the treatment outcomes of refractory patients.

To that end, FIG. 3.1 summarizes a typical embodiment of the process of single drug therapy based on the preferred EEG/QEEG method of the present invention. In the first step of the depicted example of a therapy process (step a), clinicians establish baseline parameters to measure various physiologic and behavioral changes. In step b, the medication of choice is administered to the patient in a single low dose. Dosage is increased as needed and indicated by repeat QEEG analysis and CGI scores.

Figure 5:
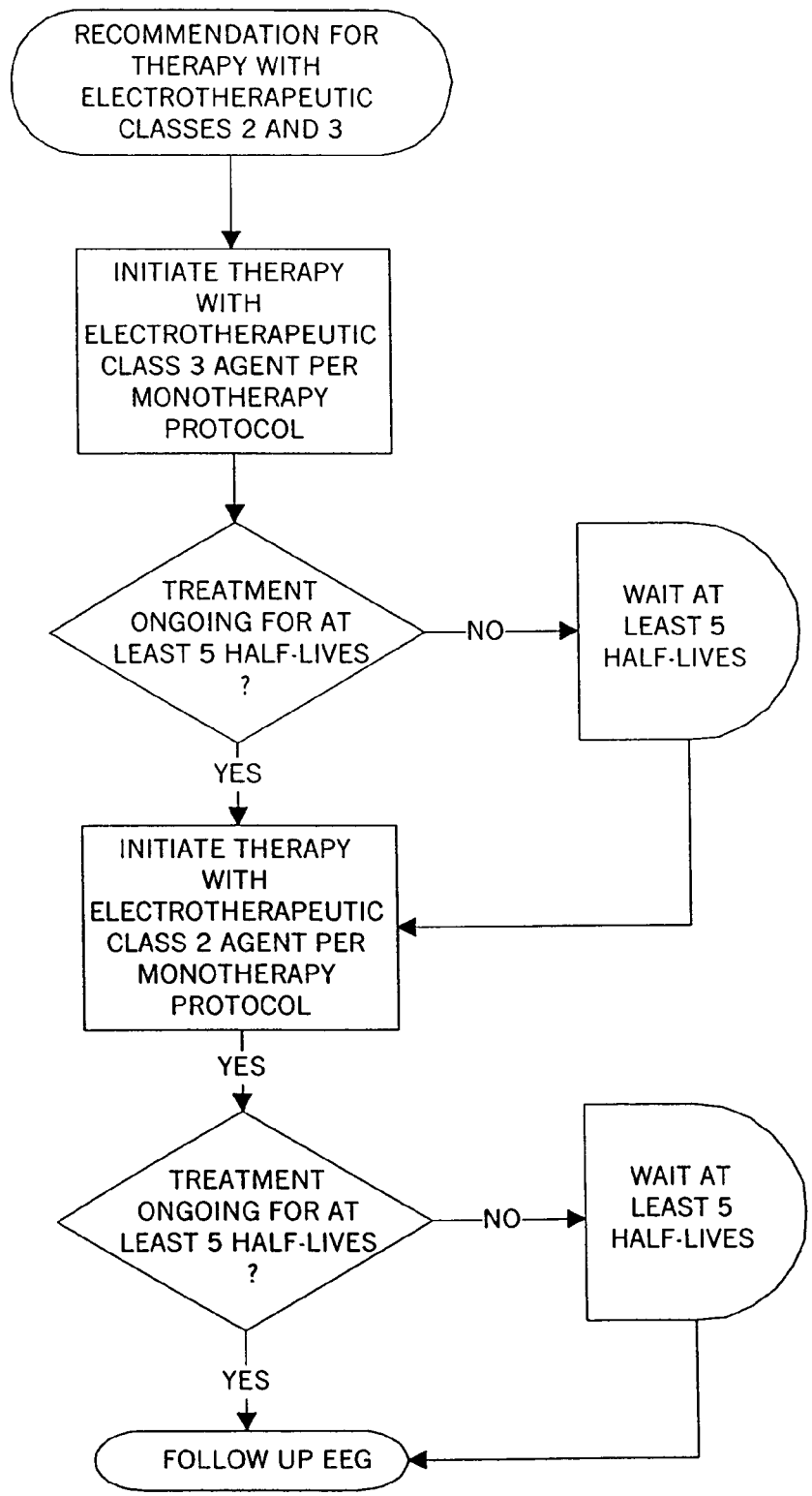
FIG. 5 depicts an algorithm for making multiple agent therapy recommendations using the method of the present invention for drugs that are in electrotherapeutic classes 2 and 3.
Figure 6:
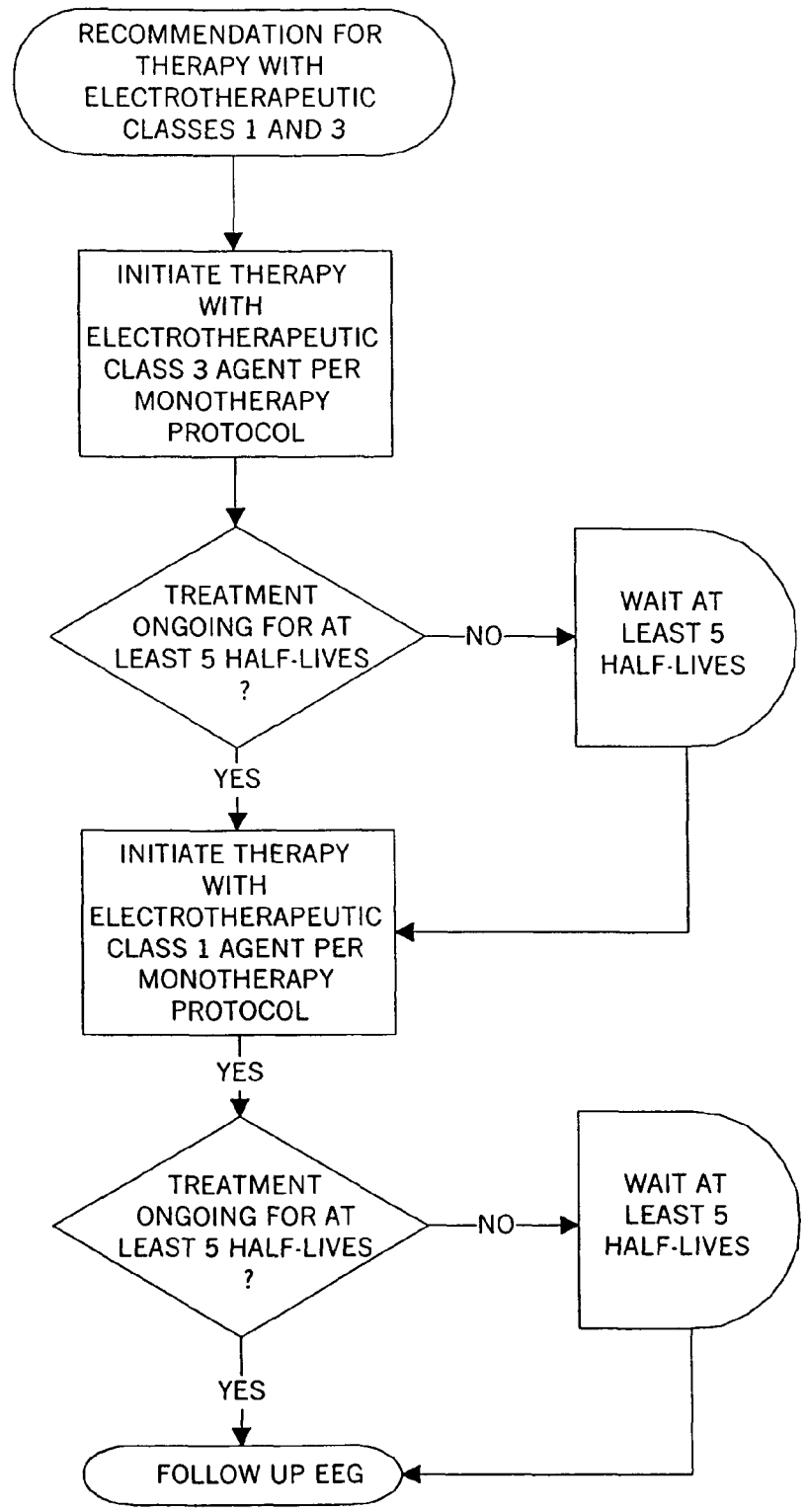
FIG. 6 depicts an algorithm for making multiple agent therapy recommendations using the method of the present invention for drugs that are in electrotherapeutic classes 1 and 3.
Figure 7:
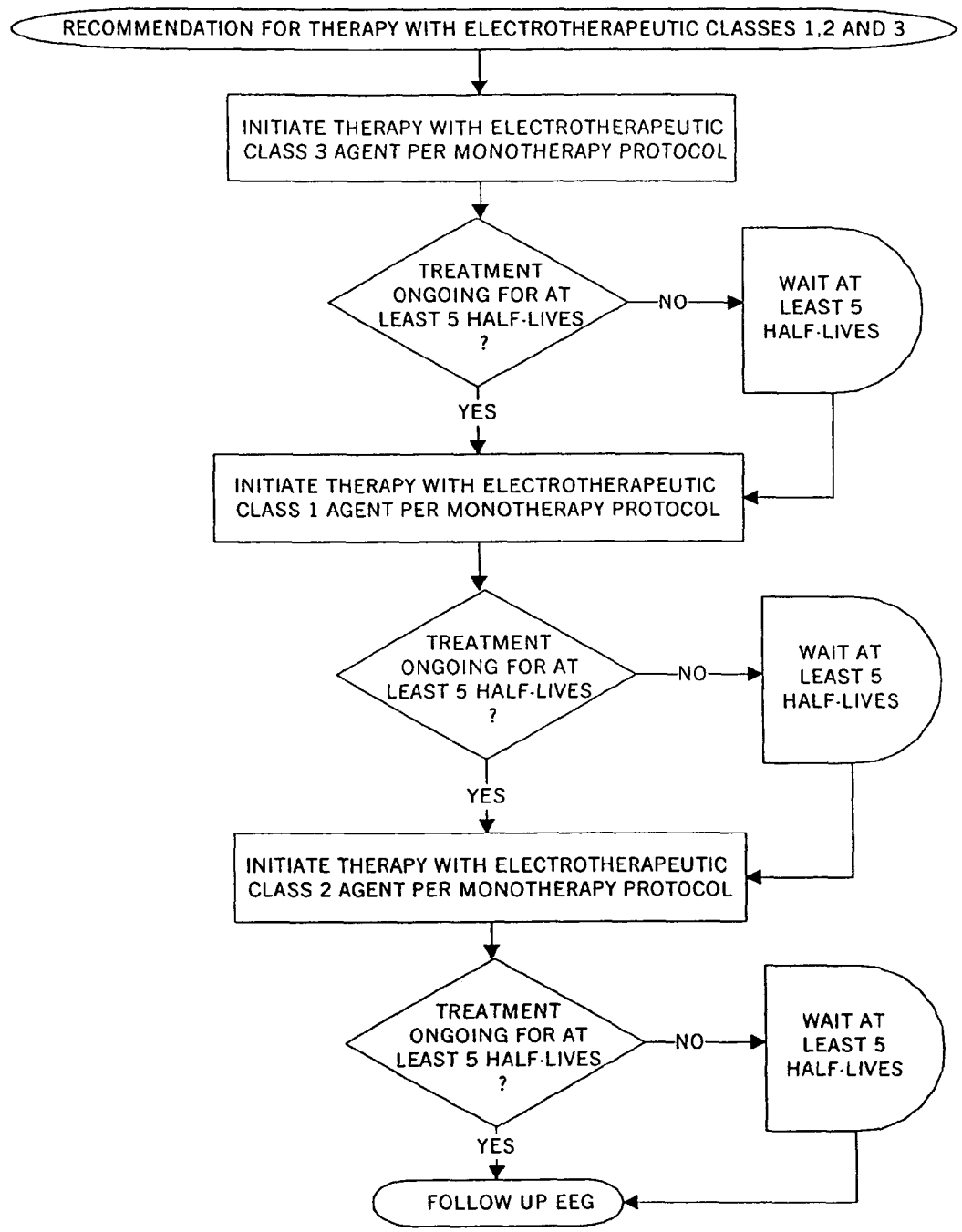
FIG. 7 depicts an algorithm for making multiple agent therapy recommendations using the method of the present invention for drugs that are in electrotherapeutic classes 1, 2, or 3.

FIG. 3.2 summarizes a typical embodiment of the process of multi-agent drug therapy based on the preferred EEG/QEEG method of the present invention. Treatment recommendations are organized according to the drug electrotherapeutic classes described earlier. A typical embodiment of a treatment recommendation involving agents in electrotherapeutic classes 1 or 2, are further summarized in FIG. 5. According to FIG. 5, step b, therapy is initiated according to the monotherapy regime (cf., FIG. 3.1) using a class 1 electrotherapeutic agent. After at least five half lives of treatment with the class 1 agent, treatment with the class 2 agent is initiated (step d). A follow-up QEEG is administered after at least five half lives of treatment with the class 2 agent (Step e). Based on the results of follow-up QEEGs and CGI scores, treatment is modified or discontinued. FIGS. 5-7 replicate similar treatment algorithms.

The method of the present invention is not a substitute for obtaining the clinical history, psychiatric assessment, medical examination and requisite laboratory studies. It augments, rather than replaces established diagnostic and treatment regimes. Medication correlations with the medication Outcomes Database of the present invention are a useful adjunct to clinical management. Determining the suitability of EEG/QEEG correlations, medication dosage, time(s) of administration, and recording of clinical outcome by symptom and behavioral rating scales remain the responsibility of the attending physician.

III. Clinical Testing Protocol for Choosing Sample Participants in Pharmacologic Drug Trials for New and Known Drugs Using EEG/QEEG The present invention also is directed to a method for screening individual human participants for inclusion in clinical drug trials of new compounds, or for known compounds for which new uses are proposed. In drug trials, the appropriate choice of study subjects assures that the findings of the trial accurately represent the drug response profile for the target population. Typically, an investigator who wants to study the efficacy of a new drug begins by creating inclusion and exclusion selection criteria that define the population to be studied. Inclusion criteria define the main characteristics of the target and accessible groups of potential test subjects. In psychiatry, the clinical characteristics that have traditionally contributed to the definition of inclusion characteristics have been based on behavioral diagnosis as outlined by the DSM, ICD, both cited earlier, or similar classification systems known to the art. In the method of the present invention, EEG/QEEG information is used in conjunction with behavioral diagnosis, as an inclusion criterion to guide sample selection.

The first step is to use behavioral diagnosis to screen potential sample subjects. Individuals without the behaviorally diagnosed pathology of interest are not considered for inclusion in the study. The second step is to choose a desired profile for study participants based on EEG/QEEG abnormality patterns and behavioral diagnosis correlates, as in the method for treating physiologic brain imbalances. The third step is to look for potential study participants with the same EEG/QEEG abnormality patterns and behavioral correlates as described earlier in the treatment methodology. The fourth step is to recruit individual participants based on their "positive" EEG/QEEG results.

The goal of this method is to structure clinical trials of new drugs or known drugs for which new uses have been indicated using "enriched" sets of test participants. The medication responsivity profiles of test participants with behaviorally defined indicia of psychopathology and related EEG/QEEG abnormalities can be accurately gauged using EEG/QEEG throughout the clinical trial period. Changes in QEEG multivariate output measurements can then be correlated with CGI scores to track drug efficacy.

IV. Method for Remote Diagnosis and Treatment Using EEG/QEEG

The present invention also relates to a method for the remote diagnosis and treatment of physiologic brain imbalances using quantified neurophysiologic information, preferably EEG/QEEG. In the method, an electronic link is typically established between a medically under served area and a center of neurophysiologic expertise, preferably EEG/QEEG expertise, using special communications software, designed to insure patient confidentiality and assist in maintaining a portion of an electronic medical record. In the context of diagnosing and treating physiologic brain imbalances, the electronic link is between a physician with digital neurophysiologic collection capabilities or a neurophysiologic recording facility and neurophysiologic information analysis center. In short, in the remote diagnosis and treatment method, a patient's neurophysiologic information is transmitted electronically without loss of resolution to an neurophysiologic information analysis center as previously presented in the diagram entitled Neurophysiologic Data Acquisition and Analysis, as depicted in FIG. 1, steps d-g, step m). The neurophysiologic information is then evaluated as described below to devise diagnosis and treatment strategies.

According to FIG. 1, the first step of the process is as described earlier for assessing and treating physiologic brain imbalances, and involves collecting neurophysiologic information from a patient and occurs at a neurophysiologic recording facility. In step f, the digitized neurophysiologic information along with additional patient identifying information is packaged using the special communications software. Packaging means the neurophysiologic information computer file(s) is/are compressed and encrypted so that it cannot be opened or examined by unauthorized personnel. The information is encrypted at the recording facility with a key known only to the neurophysiologic analysis center. The information is rigorously secured to protect the confidentiality of patient records. Patient identifying information may include the patient's name; date of birth; referring physician; handedness; height; weight; date of test; and patient social security number. This patient identifying information is algorithmically transformed as part of the encryption process. The compressed information package is then protected with an additional password.

In the step f, the compressed information files are electronically transmitted to a secure analysis site. Transmission of patient information is routinely scheduled for the early morning hours using standard file transfer protocols (FTP) via the Internet. However, "high priority" files can be immediately transferred to an analysis center for priority processing by the Site Commander software. The transmitted neurophysiologic information files are logged as they are sent, processed, and returned. All date and time log entries are Y2K compliant and are calibrated in Greenwich Mean Time (GMT). In the fourth step, the transmitted neurophysiologic information files are decompressed and decrypted at the neurophysiologic information center. The information is then analyzed according to the methods described previously.

When neurophysiologic analysis is complete, a formal report of findings is generated for the referring physician (steps l-m). The report is returned in portable document format (PDF) using commercially available software from Adobe, Inc., or the equivalent, to an neurophysiologic information transfer site. PDF files are opened and displayed using an interface to Adobe Acrobat Reader™ software or the equivalent. Reports can be printed using any operating system compatible printer but are password protected so that they cannot be modified once they leave the neurophysiologic information center.

The report includes a range of information elements, including: a professional medical interpretation of the individual patient's neurophysiologic profile; a presentation of selected features extracted by quantitative neurophysiologic analysis; a presentation of deviations from the "asymptomatic" and "symptomatic" databases; and a statement of the likelihood of favorable pharmacotherapeutic outcomes based on comparison with the Outcomes Database of patients having similar QEEG/EEG features. The formal report is designed to guide treatment strategies. However, the treating physician is ultimately responsible for medication selection, dosage titration, and side effect monitoring.

EXAMPLES

The present invention is more particularly described in the following examples which are intended for illustration purposes only, since numerous modifications and variations will be apparent to those skilled in the art.

Protocol

Collecting EEG/QEEG Information

An EEG is administered to a patient using a commercially available EEG instrument. Current suppliers of EEG instrumentation include but are not limited to Caldwell, Laboratories, Bio-Logic Systems, Inc., Nicolet Biomedical and Oxford Instruments. Electrodes are placed on the patient's scalp using the International 10/20 System convention for determining the appropriate location of the electrodes. The raw EEG information is then stored in a digital format for subsequent FFT processing.

The following patient criteria are operative for Type One Analyses. The patient must be between the ages of 6 and 90. In addition, for Type One Analysis the patient must not be undergoing drug therapy. This is because all medications may influence EEG information, giving rise to "false" outcomes. "Medications" include prescription drugs, over the counter sleeping pills, pain medication, nutritional health supplements, and megavitamins. If the patient is undergoing drug therapy, the therapy must be discontinued or avoided for seven half lives prior to the EEG test. However, the patient may be undergoing hormone replacement therapy for insulin, thyroid, progesterone, and estrogen, as well as for other hormonal deficiencies.

A variety of patients are not suitable for Type One Analysis. These include individuals who have under gone intramuscular depo-neuroleptic therapy within the proceeding twelve months. Individuals who have a history of craniotomy with or without metal prosthesis or have current unstable of seizure disorder, dementia, and mental retardation are also not candidates for Type One Analyses. Individuals who are currently using marijuana, cocaine, hallucinogens, or other illicit psychotropic compounds are not candidates for Type One Analyses. Individuals with a significant metabolic abnormality e.g. CBC, chemistry or thyroid difficulties are not candidates for Type One Analyses until these systemic processes have been normalized.

The EEG information collected from the individuals is then digitized, subjected to FFT processing, and analyzed. The first stage of analysis involves extracting a standard set of quantitative univariate measures from the FFT processed digitized EEG information. These quantitative measures include power and relative power. Power is the square of the signal amplitude, measured in microvolts squared ($\mu V^2$). Relative power measures the proportion of power in a given frequency band detected at a given electrode compared to the total band power detected at that electrode. As indicated earlier there are four EEG frequency bands of interest: delta (0.5-3.5 H); theta (3.5-7.5 H); alpha (7.5-12.5 H); and beta (12.5-35 H). The total EEG spectrum therefore runs from 0.5 to 35 H. The method of the current invention is not limited to these frequency bands and can be applied to any frequency banding.

Another standard measure extracted in the first stage of analysis is coherence. Coherence measures the similarity of activity for two scalp electrodes for all interhemispheric and intrahemispheric electrode pairs, for each of the defined frequency bands. Peak frequency measures are also computed within each frequency band. Finally, power and coherence combination measures are computed for defined sets of scalp electrodes.

Example 1

Figure 8:
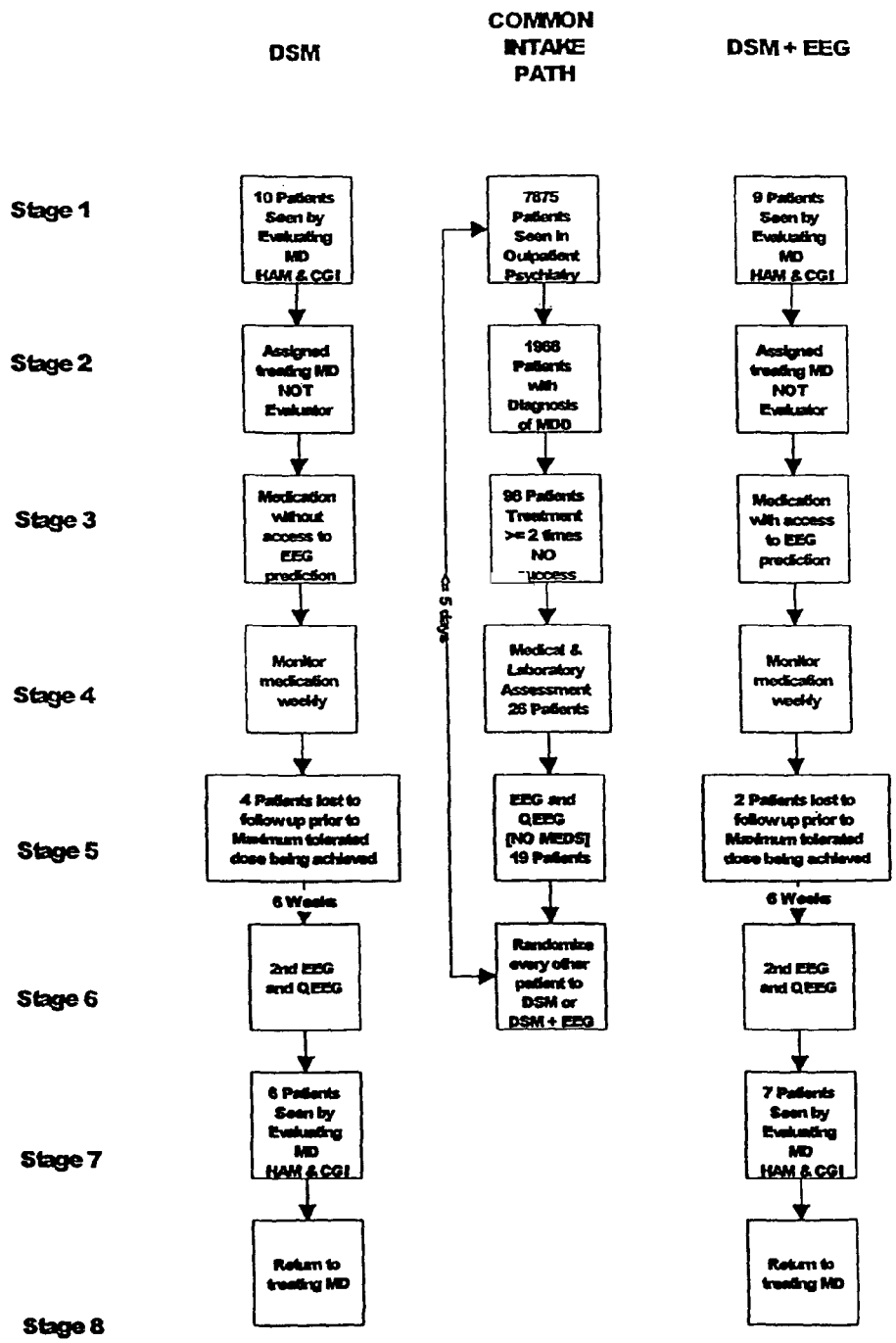
FIG. 8 depicts various medication prediction pathways for treating physiologic brain imbalances.

Guiding Drug Treatment of Patients with Manic Depressive Imbalance Using EEG/QEEG Patients with chronic Major Depressive Imbalance (MDD), determined by two senior faculty members, who had been non-responsive to at least two previous medication regimens of adequate dosage(s) and duration were accepted in the study from consecutive evaluations of outpatients at the Veterans Administration Medical Center, Sepulveda. Their lack of response to repeated previous clinical efforts provided a clear baseline from which to note any increase in treatment efficacy with EEG/QEEG information. Human Subjects Committee approval of the protocol was obtained (cf. FIG. 8). Informed consent was obtained from all study participants.

Patients were consecutively assigned to control and experimental treatment groups. Every other patient who met study criteria was treated solely on the joint decision of the treating psychiatric resident and a supervising faculty psychopharmacologist. No concurrent report of these choices was given to the staff of this study nor did the staff of this study have any part in the selection of these patients' medication. This group was called DSM DIRECTED.

A psychiatric resident and their supervising faculty psychopharmacologist, who had agreed to follow medication recommendations based on EEG/QEEG correlation, treated patients not assigned to the DSM DIRECTED group. This group was called DSM+EEG DIRECTED.

Before acceptance into the study, patients were evaluated to exclude concurrent illness. This included a physical examination with laboratory studies consisting of a hemogram, chemistry panel, thyroid stimulating hormone, urine drug screen, β-HCG (in females) and an EKG. The treating physician then interviewed patients. Hamilton-D (HAM-D) and Beck Depression (BECK) Scale scores were obtained during this interview.

After these assessments, an experienced clinician that was not and would not be involved in the treatment of the patient evaluated the patient. This initial process provided a basis for future assessment of treatment response by this clinician. This evaluating physician played no role in medication selection, had no other contact with the patient until assessing outcome of treatment, had no knowledge of which experimental group the patient belonged, nor any information on the EEG/QEEG findings. All clinical ratings present are the ratings of this clinician.

Patients taking medications other than antihypertensive or hormone replacement agents were disqualified because the control groups were selected using these criteria. Also excluded were subjects with a present or past primary psychotic diagnosis, history of intramuscular neuroleptic therapy, documented closed head injury with loss of consciousness, history of craniotomy, history of cerebrovascular accident, current diagnosis of seizure imbalance, current diagnosis of dementia, presence of mental retardation or active substance abuse.

All patients were required to be medication-free (at least seven half-lives of the longest lived medication) and illicit substance free (ascertained by a urine screen for drugs on the day of the EEG).

Patient Population

The gender and age compositions of the DSM DIRECTED group (N=6) were 4 males to 2 females, with an average age of 45. This was similar to the DSM+EEG DIRECTED group (N=7) with 5 males to 2 females and an average age of 41. Table 5 summarizes the patient population of the present study.

TABLE 5

Patient Population and Results

|  | Number of Patients | Mean/24 h in mg |
|---|---|---|
| DSM DIRECTED | | |
| Clonazepam | 1 | 1 |
| Lithium | 2 | 1200 |
| Fluoxetine | 2 | 40 |
| Nefazodone | 1 | 300 |
| Carbamazepine | 1 | 400 |
| Buspirone | 1 | 30 |
| Med/Pt Average | 1.33 | |
| DSM + EEG DIRECTED | | |
| Valproic acid | 3 | 500 |
| Lithium | 2 | 600 |
| Paroxetine | 1 | 30 |
| Fluoxetine | 3 | 30 |
| Methylphenidate | 2 | 27.5 |
| Carbamazepine | 2 | 850 |
| Sertraline | 1 | 100 |
| Med/Pt Average | 2 | |

Psychotherapy

Prior to the study, all patients were in similar types and frequency of psychotherapy, which was maintained for the duration of the study.

EEG/QEEG Information Acquisition and Analysis Procedure

Each patient had a conventional digital EEG according to the protocol given above. Twenty-one electrodes were applied according to the International 10/20 System. Then, 10 to 20 minutes of eyes-closed, awake, resting EEG was recorded on a Spectrum 32 (Cadwell Laboratories, Kennewick, Wash.), referenced to linked ears.

The conventional EEG was reviewed to exclude paroxysmal events, spikes, sharp waves, focal disturbances and other abnormalities apparent by visual inspection. Artifact-free epochs of conventional EEG, selected by a technician, were based on the rule that all artifact-free segments were to be included in the sample until at least 32 epochs of 2.5 seconds were obtained. These procedures were performed with no knowledge of which treatment group the patient had been assigned. No attempt was made to remove artifact from the EEG record using statistical techniques. During the technician's collection of EEG for quantitative analysis, when an artifact-containing portion of the record was encountered, that interval was excluded from the sample considered for quantitation. All intervals that were subjected to quantitative analysis according to the method of the invention were reviewed by the electroencephalographer/physician prior to analysis. EEG recordings were considered a priori unsuitable for quantitative analysis, due to unfavorable signal to noise ratio [less than or equal to 3:1], if average frontal power was less than 9 $\mu V_2$. No pretreatment prediction was made for these patients.

To accomplish the quantitative analysis, the sample of digitized waveforms was fast Fourier transformed into the standard EEG frequency bands of delta activity (0.5-3.5 H), theta activity (3.5-7.5 H), alpha activity (7.5-12.5 H) and beta activity (12.5-35 H). The signal features obtained for each electrode site (monopolar derivations), or across electrode pairs (bipolar derivations) included absolute power, relative power, coherence, frequency, and symmetry. EEG information was log transformed to obtain Gaussianity, age-regressed and transformed according to the multivariate Z score profiling method of the invention. This produced measures of each study patient's EEG deviation from a database of age-matched referential EEG's collected from asymptomatic individuals from 6 to 90 years of age. A differential eye channel was used for the detection of eye movement. All impedances were less than 5,000 ohms. The EEG amplifiers had a band pass from 0.5 to 70 H (3 dB roll off per octave). A 60 H notch filter was used during the collection process.

Method of Classifying EEG/QEEG Medication Response

A database of medication-free patients containing EEG/QEEG findings and subsequent medication outcomes compiled in our laboratory over the past eight years was used for deriving the medication response predictions. A rule-based classifier using the current patient's neurophysiologic information profile as described above and the database from the inventor's patient population was used to review pretreatment EEG/QEEG information from each study patient. An EEG/QEEG specific medication outcome prediction, containing the correlated medication responses of antidepressant, anticonvulsant and stimulant classes was reported to the patient control officer. This information was distributed only to the treating physician of the individual DSM+EEG DIRECTED patient, as described above. Medication outcome predictions for all other patients were sealed until the end of the study.

Figure 9:
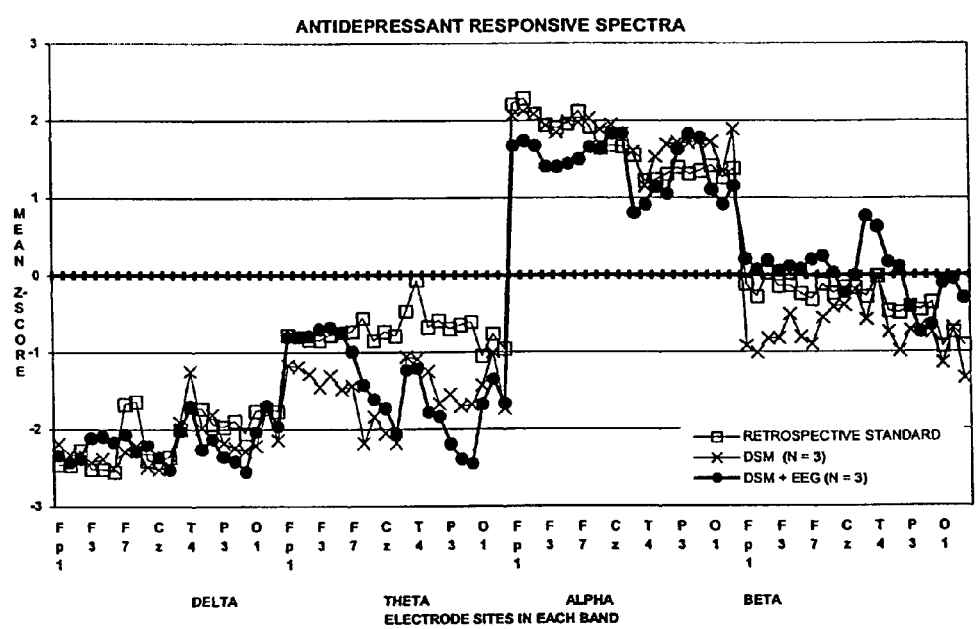
FIG. 9 depicts a composite QEEG antidepressant responsive spectrum.

An antidepressant responsive spectrum identified in previous studies was incorporated in the rule-based classifier used to predict antidepressant responsivity for all patients in the present study. FIG. 9 depicts the average relative power spectrum of sixty patients with affective and attentional imbalances that were antidepressant responsive. This spectrum demonstrates global delta frequency deficit from −2.5 to −1.8 mean-units extending posteriorly, a diffuse theta deficit trend of −0.8 to −1.0 mean-units sparing the temporal regions, a +2.3 mean-units alpha maximum in the frontal polar region and a second alpha maximum of +2.1 mean-units in the posterior frontal region. These maxima are accompanied by a relative alpha minimum of +1.2 mean-units in the temporal region and sustained posterior alpha excess.

Figure 10:
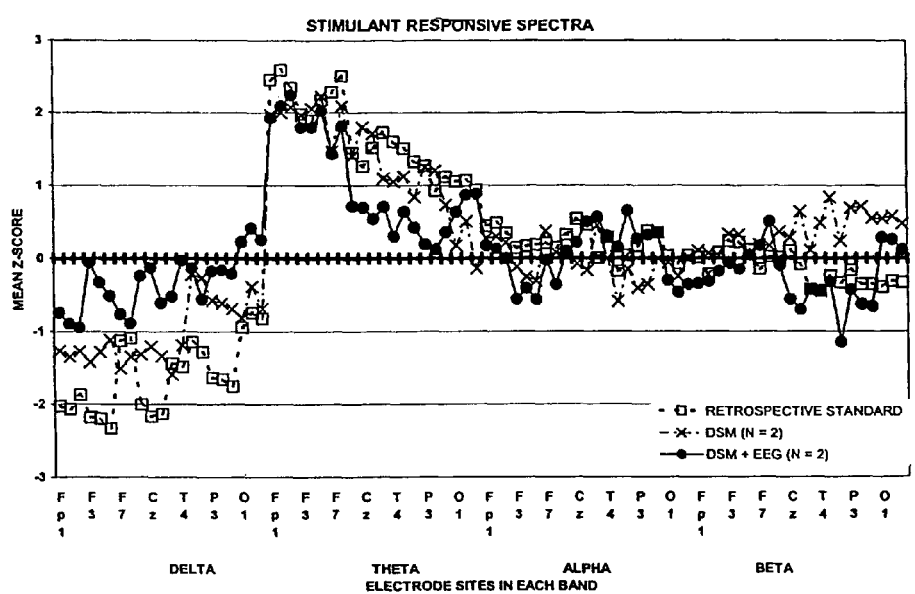
FIG. 10 depicts a composite QEEG stimulant responsive spectrum.

A stimulant responsive spectrum identified in previous studies was incorporated in the rule-based classifier used to predict stimulant responsivity for all study patients. FIG. 10 depicts the average relative power spectrum of twenty-one patients with affective and attentional imbalances that were stimulant responsive. This spectrum exhibited a frontal polar delta frequency deficit from −2.0 to −2.3 mean-units. There were two frontal maxima in the theta band at +2.6 and +2.5 mean-units. The theta frequency showed +1.7 mean-units excess in the temporal region, gradually diminishing posteriorly toward +0.9 mean-units. The alpha and beta bands of this spectrum were distributed about a mean-score of zero.

Figure 11:
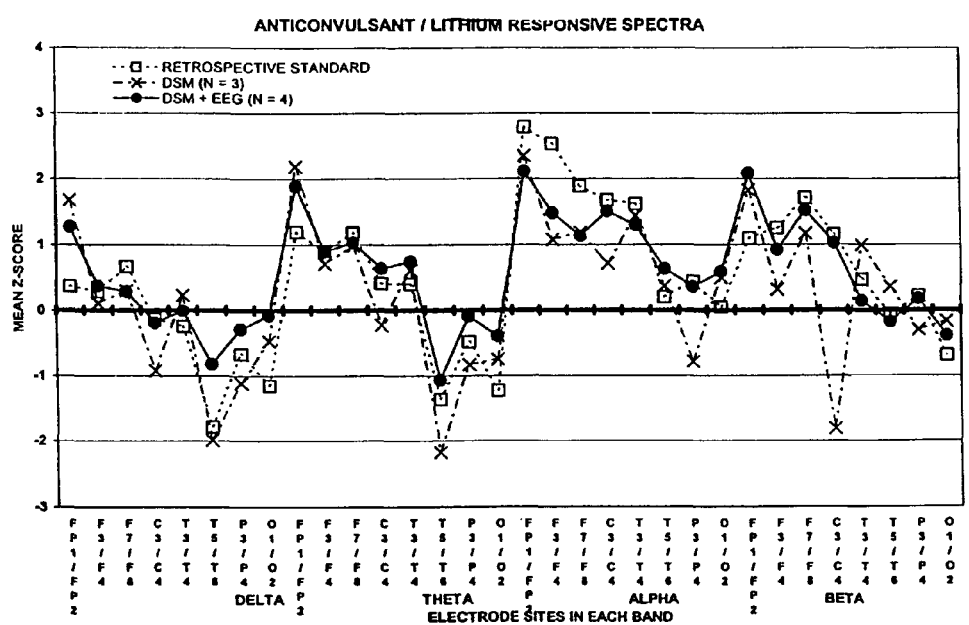
FIG. 11 depicts a composite QEEG anticonvulsant lithium/responsive spectrum.

An anticonvulsant/lithium responsive spectrum identified in previous work was incorporated in the rule-based classifier used to predict anticonvulsant/lithium responsivity for all study patients. FIG. 11 depicts the average interhemispheric coherence spectra of twenty-six patients with affective and attentional imbalances indicated anticonvulsant and or lithium responsivity. The spectra exhibited posterior delta hypocoherence (up to −1.7 mean-units), posterior theta hypocoherence (up to −1.4 mean-units), frontal alpha hypercoherence (up to +2.9 mean-units), and frontal beta hypercoherence (up to +1.7 mean-units).

Clinical Monitoring

The treating physician and their faculty supervisor for both experimental groups monitored treatment in weekly follow-up sessions. The mean follow-up for the study groups was 25 weeks. After six weeks on medication(s) at maximal tolerated dosage, treatment efficacy was assessed by the independent evaluating physician, blind to patient status [DSM DIRECTED or DSM+EEG DIRECTED] and medication regimen, who had assessed the patient prior to treatment. This physician's prior knowledge of the patient permitted the use of Clinical Global Improvement (CGI) ratings. A CGI score of zero indicated no improvement, 1 indicated mild improvement, 2 indicated moderate improvement and 3 indicated marked improvement or no residual symptoms. A CGI rating equal to, or greater than 2 levels was required to qualify as improved.

Results

Neurometric Spectral Features

Two patients, one each in the DSM DIRECTED and DSM+EEG DIRECTED groups, had EEG records that exhibited an average frontal power of less than 9 $\mu V^2$. No EEG/QEEG medication prediction was made for these patients.

The remaining eleven patients were classified into EEG/QEEG sets based on objective spectral features. EEG/QEEG sets included relative theta frequency excess (the percentage of total power contributed by the theta frequency band in excess of that expected from the age-matched reference population previously noted), relative alpha frequency excess (the percentage of total power contributed by the alpha frequency band in excess of that expected) and interhemispheric hypercoherence and hypocoherence (synchronization of electrical activity in homologous brain regions, separately for each frequency band and for the entire spectrum).

The average relative power spectra of antidepressant responders in both the DSM DIRECTED (N=4) and DSM+EEG DIRECTED (N=3) treatment groups were compared. The spectra included global delta frequency deficits of −2.2/−2.4 mean-units to −2.1/−2.0 mean-units extending posteriorly. There were fronto-central theta deficits of −2.1/−1.6 mean-units with temporal sparing and sustained posterior theta deficits of up to −1.7/−2.4 mean-units. In the alpha band these spectra show frontal polar maxima's of +2.1/+1.7 mean-units.

The average relative power spectra of stimulant responders in both the DSM DIRECTED (N=2) and DSM+EEG DIRECTED (N=2) treatment groups were compared. These spectra included irregular frontal delta frequency deficits up to −1.4/−0.9 mean-units. Theta excess in the frontal region was +2.2/+2.2 mean-units. Theta excesses attenuate posteriorly. Alpha and beta relative powers are distributed about a mean-score of zero.

The average coherence spectra of anticonvulsant or lithium responders in both the DSM DIRECTED (N=3) and DSM+EEG DIRECTED (N=4) treatment groups were compared. The spectra exhibited frontal delta frequency hypercoherence of +1.7/+1.3 mean-units, posterior delta frequency hypocoherence of up to −2.0/−0.8 mean-units, frontal theta hypercoherence of +2.2/+1.9 mean-units, frontal alpha hypercoherence of +2.3/+2.1 mean-units, and frontal beta hypercoherence of +1.8/+2.1 mean-units.

Main Outcome Measures

Medication Regimens

Table 5 shows the medications were prescribed in recommended doses and plasma medication monitoring was conducted and maintained within therapeutic range for valproate, carbamazepine and lithium.

HAM-D and BECK Behavioral Outcome Sets

The HAM-D for the DSM DIRECTED group showed a mean pretreatment score of 24 compared to a mean treatment score of 18. The BECK Scale showed a mean pretreatment score of 22 compared to a mean treatment score of 20. The HAM-D for the DSM+EEG DIRECTED group showed a mean pretreatment score of 23 compared to a mean treatment score of 9. The BECK Scale showed a mean pretreatment score of 26 compared to a mean treatment score of 13. These changes in test scores between the two treatment groups are highly significant (Friedman ANOVA $\chi2(N=^{13};\ df=3)$ $p<0.009$).

Clinical Global Improvement Ratings

In the DSM+EEG DIRECTED group 6 of 7 patients had a CGI change of 2 or more; additionally 4 of 7 of these patients achieved a CGI of 3 indicating no evidence of illness. In the DSM DIRECTED group 1 of 6 patients had a CGI change of 2 or more and 5 of 6 patients had a CGI change of 0 indicating no improvement ($p=0.02$; Fisher's exact).

EEG Outcome Sets

All but one patient (low power) in the DSM DIRECTED group had medication outcome predicted from pretreatment EEG/QEEG information, but this information was not reported to the treating physicians. When the study finished, the prediction was examined with respect to the patient's clinical response.

All patients in the DSM DIRECTED group were predicted from their EEG/QEEG study to be nonresponsive to the physicians' medication selections. DSM+EEG DIRECTED patients were treated with the agents that were predicted by EEG/QEEG information to produce a favorable clinical outcome. Six of seven patients in this group responded as predicted a priori by EEG/QEEG information. When the positive and the negative a priori predictions are combined, ten out of eleven predictions were correct ($p=0.015$; Fisher's exact). These information are associated with an 86 percent likelihood of positive patient outcome with each prediction and Youdin Index of 0.8 (Youden W J. Index for rating diagnostic test. Cancer 1950; 3: 32-35).

Discussion

Patients treated in the DSM DIRECTED group had an inferior response to pharmacotherapy. Only one of six patients demonstrated improved behavioral and clinical outcome measurements by HAM-D, BECK and CGI ratings. In comparison, six of seven patients in the DSM+EEG DIRECTED group responded with significantly improved HAM-D, BECK and CGI ratings. Furthermore, remission of symptoms or a CGI rating of 3 was achieved by four of seven patients in the DSM+EEG DIRECTED group. These therapeutic improvements would be unanticipated given the chronic and refractory nature of the imbalance in this select population Pharmacotherapeutic choices in the DSM+EEG DIRECTED paradigm differed substantially from the control group by demonstrating initial combination pharmacotherapy with anticonvulsant/anticyclic agents and stimulants. With behavioral based treatment algorithms, these medication classes are recommended for pharmacotherapy of MDD only after failures of antidepressant class agents has labeled a patient refractory. Differences in selection of type of agent and number of agents used in initial treatment by the two groups are striking. Selection of monotherapy in the absence of objective EEG/QEEG information reveals a clear bias of the clinicians. A sequential strategy was supported and encouraged by numerous current reports (See Sharan S P, Saxena S. Treatment-resistant depression: clinical significance, concept and management. *Natl. Med J India* March-April 1998; 11(2):69-79; Thase M E, Rush A J. When at first you don't succeed: sequential strategies for antidepressant nonresponders. *J Clin Psychiatry* 1997, 58 Suppl 13:23-9; Nelson J C. Treatment of antidepressant nonresponders: augmentation or switch? *J Clin Psychiatry* 1998, 59 Suppl 15:35-41). Augmentative strategies are also supported but only as a secondary approach (Shelton R C, Treatment options for refractory depression. *J Clin Psychiatry* 1999, 60 Suppl 4:57-61; discussion 62-3; Thase M E, Howland R H, Friedman E S. Treating antidepressant nonresponders with augmentation strategies: an overview. *J Clin Psychiatry* 1998, 59 Suppl 5:5-12; Heit S, Nemeroff C B. Lithium augmentation of antidepressants in treatment-refractory depression. *J Clin Psychiatry* 1998, 59 Suppl 6:28-33; Nierenberg A A, Dougherty D, Rosenbaum J F. Dopaminergic agents and stimulants as antidepressant augmentation strategies. *J Clin Psychiatry* 1998, 59 Suppl 5:60-3; Dougherty D, Rosenbaum J F, Joffe R T. Refractory depression: treatment strategies, with particular reference to the thyroid axis. *J Psychiatry Neurosci* Nov. 22, 1997(5):327-31). The diagnoses of the clinicians treating the DSM DIRECTED patients and lacking electrophysiological information was consistent with current recommended treatment pathways.

Outcome prediction from EEG/QEEG information correlated with symptomatic behavioral assessments—CGI ratings, HAM-D and BECK scores. A priori identification of both non-response and response to particular pharmacotherapies suggests that EEG/QEEG information can reduce iatrogenic morbidity by correlating medication selection with the distribution of physiological response in MDD. Such an understanding adds clarity to the definition of "treatment non-responsive" and "treatment resistant", namely unsuccessful matching of medication to a particular pathophysiology.

This study shows that medication response in refractory MDD patients can be predicted by EEG/QEEG information. The prognostic ability of pretreatment EEG/QEEG information with respect to pharmacotherapeutic outcome in this population is consistent with previously reported retrospective associations of EEG/QEEG measurements and psychiatric medication response. Also demonstrated is the ability of psychiatric physicians to incorporate EEG/QEEG information with medication correlation as a laboratory test in clinical practice. The DSM+EEG paradigm allows physicians to select medications which were associated with improved patient outcomes.

Example 2

Method for Assessing Physiologic Brain Imbalances and Predicting Pharmacoresponsivity Using EEG/QEEG Patients with DSM-III-R diagnoses of 296.xx, 311.00, and 314.xx were prospectively enrolled in a study from consecutive evaluations of a largely (>90%) Caucasian, suburban, population seeking care in a fee for service environment. Patients were evaluated as given below, and treated according to current clinical practice. Retrospective analyses of the relationships between clinical responsivity and neurophysiologic features were performed in order to identify those neurophysiologic features associated with unsuccessful and successful outcomes of pharmacotherapy.

Two samples of medication-free (no medicine for seven half-lives of the longest half-life agent) patients: those with affective imbalance diagnoses (296.xx or 311.00) and those with attentional imbalance diagnoses (314.xx) were identified by historic and clinical examination. These diagnoses were then confirmed in review by a second experienced clinician. One hundred and three (103) consecutive individuals were included in the study from those patients who were considered appropriate for the testing procedure. Subsequent to the Neurometric testing, patients were excluded from the study if laboratory results (Chem. 24, CBC, TSH, UDS, and HCG) were not available or there was not follow-up for at least six months after the initiation of pharmacotherapy. These criteria eliminated 2 patients with attentional imbalances and 1 patient with affective imbalance.

The attentional disordered sample consisted of 46 patients, 34 males and 12 females, with a mean age of 12.4 years. The affectively disordered population consisted of 54 patients, 20 males and 34 females, with a mean age 13.5 years in the adolescent population and a mean age of 40.4 years in the adult population.

Fifty percent of the attentionally disordered population had not been previously diagnosed or treated for their attentional problems, despite chronic complaints and long-standing behavioral aberrations. The other half of this population was previously diagnosed and classified as treatment refractory by the referring clinician. In the affective disordered population there was a four-fold excess of unipolar patients by DSM-III-R criteria. Only one adolescent received the diagnosis of Bipolar Imbalance.

EEG Information Acquisition and Analysis

Using the international 10/20 system of electrode placement, twenty-one paste-on electrodes were applied to the scalp. Eyes closed resting EEG was recorded on a Cadwell Spectrum 32, referenced to linked ears, allowing for retrospective montage analysis of all information.

After examining the EEG record, a minimum of thirty-two 2.5 second epochs of artifact-free EEG were selected and subjected to quantitative analysis according to the method of the present invention including absolute power, relative power, power asymmetry, mean frequency, and coherence for the delta (1.5-3.5 H), theta (3.5-7.5 H), alpha (7.5-12.5 H), and beta (12.5-35 H) frequency bands. These measurements were logarithmically transformed to obtain Gaussianity, age-regressed, and transformed relative to population norms. A differential eye channel was used for the detection of eye movement. All electrode impedances were less than 5,000 ohms. The EEG amplifiers had a band pass from 0.5 to 70 H (3 dB points), with a 60 H notch filter.

Clinical Monitoring

Treatment was monitored in weekly, bimonthly, or monthly follow-up sessions using Clinical Global Improvement (CGI) ratings. CGI's taken from the patient's baseline presentation were generated using information gathered from parent and teacher Conner's scales, patient and parent interviews, contact with teachers, and the treating clinician's assessment for the attentionally disordered population. CGI's were rated on a 4 point scale, with 0=no improvement, 1=minimal improvement, 2=moderate improvement, and 3=marked improvement or no evidence of illness. A similar process was used in rating the affectively disordered population, but without the consideration of Conner's scales in deriving the CGI ratings.

Treatment Selection

The protocols were as follows. The attentional deficit population was initially treated with a stimulant medication, principally methylphenidate at a dose not exceeding 1.0 mg/kg body weight per day. If the patient did not achieve a Clinical Global Improvement score of 2 (moderate global improvement) or 3 (marked global improvement) after one month of medication, the stimulant was discontinued and secondary treatment with an antidepressant medication was initiated. If the patient did not achieve a Clinical Global Improvement score of 2 or 3 after six weeks of medication, the antidepressant was augmented with tertiary treatment consisting of an anticonvulsant (carbamazepine, valproic acid) or stimulant.

Affectively disordered patients without a history of mania were initially treated with a heterocyclic antidepressant (up to 3.0 mg/kg/day) or a serotonin re-uptake inhibitor antidepressant. If by six weeks the patient did not achieve a Clinical Global Improvement score of 2 or 3, they received secondary treatment with anticonvulsant (carbamazepine, valproic acid) or lithium. Failure to improve after three weeks at therapeutic plasma levels caused tertiary measures to be instituted, most frequently a stimulant challenge with methylphenidate. If the challenge demonstrated stimulant responsivity a therapeutic trial of stimulant was added to the patient's regimen.

Results

Neurometric Spectral Features

Figure 12:
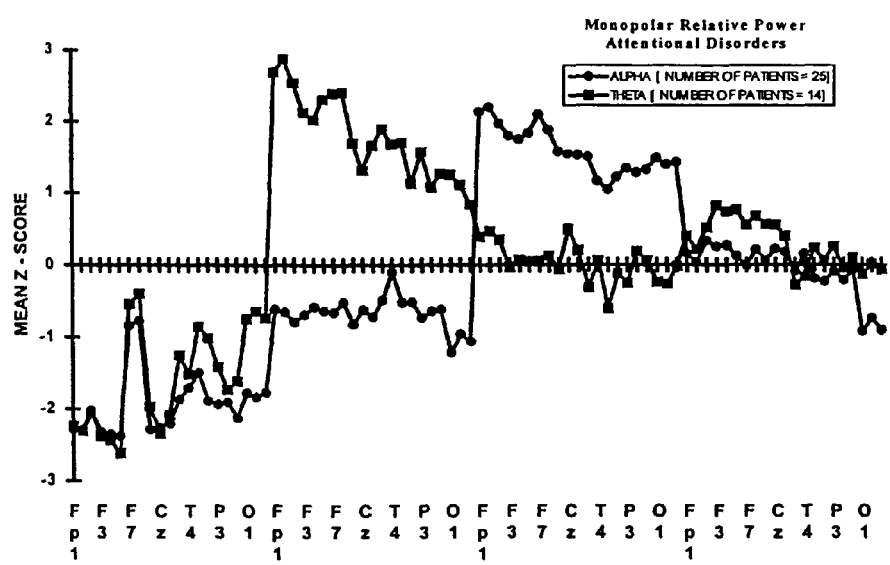
FIG. 12 depicts a composite QEEG spectrum of patients treated for attentional disorders.
Figure 13:
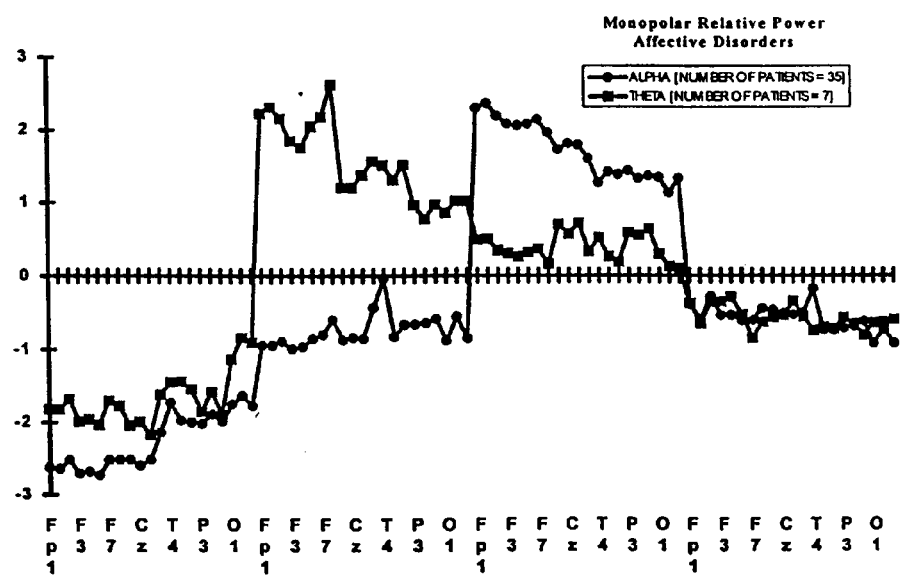
FIG. 13 depicts a composite QEEG spectrum of patients treated for affective disorders.

The population was heuristically divided into four groups based on objective spectral features. These groups included those who exhibited, respectively, relative alpha frequency excess, relative theta frequency excess, inter-hemispheric hypercoherence, or patients whose neurophysiologic spectra did not demonstrate one of the preceding profiles. These Neurometric profiles could be identified within both attentionally disordered and affectively disordered patients, as can be seen in FIGS. 12 and 13, where the theta excess and alpha excess groups with each diagnostic category were easily distinguished. In addition, the striking electrophysiologic similarity of the under and over eighteen year old affectively disordered groups shown in FIG. 14 demonstrated a robustness of these findings across ages. It was further noted that all these groups share the feature of delta frequency relative power deficit.

In FIG. 12, the theta excess subgroup of attentional disordered patients demonstrated a spectrum with global delta frequency deficit, a +2.7 mean-units theta maxima in the frontal polar region, and a smaller but significant theta excess of +2.3 mean-units in the posterior frontal region. These maxima accompanied a relative theta minima in the central region, and a theta relative power decrease posteriorly. In contrast, the alpha excess subgroup of attentional disordered patients demonstrated a spectrum with global delta frequency deficit, a +2.1 mean-units alpha maxima in the frontal polar region and a second alpha maxima of +2.0 mean-units in the posterior frontal region. These maxima were then accompanied by a relative alpha minima in the temporal region, and an alpha relative power increase posteriorly. Twenty-five percent (25%) of the attentional disordered patients demonstrated inter-hemispheric hypercoherence primarily in the frontal region.

FIG. 13 indicates that the theta excess subgroup of affectively disordered patients demonstrated a spectrum with global delta frequency deficit, a theta maxima of +2.2 mean-units in the frontal polar region, a second theta maxima of +2.4 mean-units in the posterior frontal region, and a decrease of relative theta power posteriorly. The alpha excess subgroup of affectively disordered patients demonstrated a spectrum with global delta frequency deficit, alpha maxima of +2.2 mean-units in the frontal polar region, a broad frontal alpha plateau of approximately +2.0 mean-units, and a second smaller alpha relative power plateau posteriorly of +1.0 mean-unit. Inter-hemispheric hypercoherence was seen in thirty-six percent (36%) of the affectively disordered adolescent and fifty-seven percent (57%) of the adult groups, mainly between the frontal regions.

Figure 14:
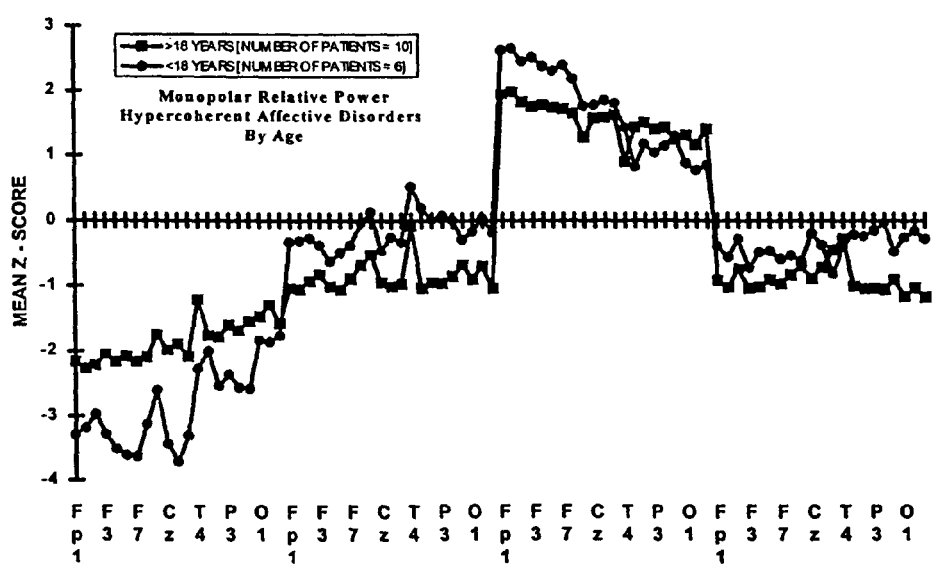
FIG. 14 depicts a composite QEEG spectrum of patients by age, treated for affective disorders.

FIG. 14 depicts the examination of the relative power spectrum as a function of age in affectively disordered patients who also exhibited inter-hemispheric hypercoherence found similar delta frequency power deficits in the two age groups. The under eighteen year-old group deficit was minimally 1 unit larger than the adult population. In the alpha frequency region of FIG. 14, the under eighteen year-old group exhibited maximal relative power in the frontal polar region where it reached a mean of +2.6 mean-units. This maxima was followed by an alpha plateau of approximately +2.2 mean-units in the remaining portions of the frontal region. The adult affectively disordered spectrum showed qualitatively similar distributions with an alpha plateau of +1.8 mean-units in the frontal region.

The relative frequency of each of these electrophysiologic subgroups differs across these DSM-III-R diagnostic categories and by age, as can be seen in Table 6. These Neurometric subgroup frequency distributions are statistically significant for both imbalances and both age groups of the affectively disordered patients ($X^2$ df=2, p<0.01). It was noted that for both DSM-III-R diagnoses the largest percentage of the groups share a neurophysiologic alpha excess profile.

TABLE 6

Neurometric Subgroups in Attentionally and Affectively Disordered Patients

| DSM-III-R Diagnostic Categories | FRONTAL ALPHA EXCESS | OTHER | FRONTAL THETA EXCESS |
|---|---|---|---|
| Attentionally Disordered | 25 [54%] | 7 [15%] | 14 [31%] |
| Affectively Disordered under 18 Years Old | 18 [72%] | 4 [16%] | 3 [12%] |
| Affectively Disordered 18 Years and Older | 17 [58%] | 8 [29%] | 4 [13%] |

Outcome Sets

At six months after the initiation of treatment CGI ratings for the frontal alpha and theta excess subgroups were divided into treatment responsive and treatment refractory as shown in Tables 7 and 8.

TABLE 7

Clinical Response of DSM-III-R Affective Disorders by Neurometric Subgroup

| | FRONTAL ALPHA EXCESS | FRONTAL THETA EXCESS |
|---|---|---|
| RESPONSIVE | 30 [86%] | 2 [29%] |
| NON RESPONSIVE | 5 [14%] | 5 [71%] |

The affective disordered population of Table 7 with frontal alpha excess was responsive 86% of the time to the treatment paradigm ($X^2$ df=1, p<0.001) while the affective disordered population with frontal theta excess was responsive 29% of the time ($X^2$ df=1, p=<0.26), not a significant difference.

Similarly the attentionally disordered population of Table 8 with frontal alpha excess was responsive 80% of the time to the treatment paradigm ($X^2$, df=1, p<0.003) while the attentional disordered population with frontal theta excess was responsive 71% of the time ($X^2$ df=1, p=0.1), not a significant difference. The non-responsive category also contained three affectively disordered patients and two attentionally disordered patients who were not compliant with pharmacotherapy. The treatment responsive category consisted of those patients with CGI's of 2 (26 patients –42%) or 3 (36 patients –58%).

TABLE 8

Clinical Response of DSM-III-R Attentional Disorders by Neurometric Subgroup

| | FRONTAL ALPHA EXCESS | FRONTAL THETA EXCESS |
|---|---|---|
| RESPONSIVE | 20 [80%] | 10 [71%] |
| NON RESPONSIVE | 5 [20%] | 4 [29%] |

Clinical response was analyzed as a function of neurophysiologic spectral findings and class(es) of pharmacotherapeutic agent(s) for the normocoherent groups as shown in Table 9. The frontal alpha excess/normocoherent subgroup was 87% or more responsive to antidepressants without regard to the patient's clinical presentation with attentional or affective symptoms. The frontal theta excess/normocoherent subgroup appeared only in the attentionally disordered clinical population. In that population it was 100% responsive to stimulants.

TABLE 9

Pharmacoresponsivity of Normocoherent Clinical Populations

| | FRONTAL ALPHA EXCESS RESPONSIVE TO ANTIDEPRESSANTS | FRONTAL THETA EXCESS RESPONSIVE TO STIMULANTS |
|---|---|---|
| AFFECTIVELY DISORDERED | 9/10 [90%] | 0 [0%] |
| ATTENTIONALLY DISORDERED | 13/15 [87%] | 7/7 [100%] |

Clinical response as a function of neurophysiologic spectral findings and class(es) of pharmacotherapeutic agent(s) for the hypercoherent populations as shown in Table 10. Here, the frontal alpha excess/hypercoherent subgroup was 85% or more responsive to anticonvulsants/lithium without regard to the patient's clinical presentation with attentional or affective symptoms. The frontal theta excess/hypercoherent subgroup represented only a total of 5 patients, 4 of whom (80%) were responsive to anticonvulsants.

TABLE 10

Pharmacoresponsivity of Hypercoherent Clinical Populations

| | FRONTAL ALPHA EXCESS RESPONSIVE TO ANTICONVULSANTS/Li | FRONTAL THETA EXCESS RESPONSIVE TO ANTICONVULSANTS |
|---|---|---|
| AFFECTIVELY DISORDERED | 17/20 [85%] | 2/2 [100%] |
| ATTENTIONALLY DISORDERED | 5/5 [100%] | 2/3 [67%] |

Discussion

As the findings demonstrate, the patient samples in each of the DSM-III-R diagnostic categories studied were not neurometrically homogeneous. Neurometrically distinguishable subgroups were present within each category; moreover, the Neurometric subgroups were qualitatively similar across the DSM-III-R diagnostic categories. The relative frequency of the subgroups differed between the categories examined as well as between age groups within the affectively disordered population. It is important to note that the Neurometric subgroups in the affectively disordered patients were qualitatively similar independent of the patient's age, demonstrating the existence of electrophysiologic similarities between childhood and adult affective imbalances.

Retrospective analyses of clinical outcomes as a function of Neurometric subgroup membership demonstrate differential responsivity to selected classes of pharmacologic agents. The design of the clinical treatment paradigm for these different DSM-III-R categories might be expected to prejudice the findings because they should produce groups of affectively disordered patients with a high frequency of response to antidepressants and an attentionally disordered population with a high frequency of response to stimulants; however, the outcomes show that subgroups with similar neurophysiologic features responded to the same class of psychopharmacological agent despite the impact of the clinical treatment paradigm and the DSM-III-R classification of the patient's presenting problems. That is, the presence of the excess frontal alpha Neurometric pattern was associated with responsivity to antidepressant class pharmacotherapy whether it appeared in a patient with DSM-III-R behavioral features consistent with depressive imbalances or in a patient with DSM-III-R behavioral features consistent with attentional imbalances. Other quantitative electrophysiologic studies have shown that the serotonin reuptake inhibitors decrease alpha abundance (Saletu B, Grunberger J. Classification and Determination of Cerebral Bioavailability of Fluoxetine: Pharmaco-EEG, and Psychometric Analyses. *Clinical Psychiatry* 1985; 46:45-52; Itil T, Itil K, Mukheijec S, Dayican G, Shaw G. A Dose-Finding Study with Sertraline, a New 5-HT Reuptake Blocking Antidepressant Using Quantitative Pharmaco-EEG and Dynamic Brain Mapping. *Journal of Integrative Psychiatry* 1989; 7:29-39). This finding is consistent with our finding that the excess frontal alpha/normocoherent patient subgroup was highly responsive to the antidepressant class of medications.

In this study, it was also found that patients with hypercoherent Neurometric patterns responded to anticonvulsant/lithium class agents without regard to DSM-III-R diagnosis. These findings demonstrate the clinical utility of the Neurometric method of QEEG with its ability to define alpha frequency and coherence abnormalities not appreciated in qualitative electroencephalography.

Our information suggests that this population was made responsive by the addition of anticonvulsants or lithium. The recognition of a physiologic feature common to this subgroup of treatment resistant schizophrenic, affective, and attentional disordered patients, which appears to specify the need for augmented pharmacotherapy, has clinical impact in the reduction of morbidity. This technology may obviate sequential agent trials toward justifying combined pharmacotherapies by indicating combined pharmacotherapy at the onset of treatment.

The theta excess population could be divided into two subtypes: a frontal theta excess group and a global theta excess group. The frontal theta excess group responded to stimulants. The global theta excess group responded to anticonvulsant agents. The findings are consistent with the common clinical experience of heterogeneous responses to classes of pharmacologic agents in DSM-III-R diagnostic categories.

What is claimed is:

1. A method for determining medication efficacy, comprising:
    a) providing;
        i) a patient having a physiologic brain imbalance, wherein said imbalance is identified using a first electroencephalography recording, and
        ii) a medication; and,
    b) converting said first electroencephalography recording to at least one first multivariate outcome measurement wherein said first outcome measurement comprises a plurality of first univariate Z scores, wherein said first multivariate outcome measurement is derived from a frequency band selected from the group consisting of delta, theta, alpha, and beta;
    c) administering said medication to said patient;
    d) obtaining a second electroencephalography recording from said patient and converting said second electroencephalography recording to at least one second multivariate outcome measurement wherein said second outcome measurement comprises a plurality of second univariate Z scores, wherein said second multivariate outcome measurement is derived from a frequency band selected from the group consisting of delta, theta, alpha, and beta; and
    e) comparing said first multivariate outcome measurement with said second multivariate outcome measurement wherein a differential change between said first and second measurement determines said medication efficacy.

2. The method according to claim 1, wherein said comparing further comprises using a reference database.

3. The method according to claim 1, wherein said difference between said first multivariate outcome measurement and second follow-up multivariate outcome measurement is proportional to the efficacy of said medication.

4. The method of claim 1, wherein said delta frequency band comprises a first set of univariate measurements selected from the group consisting of absolute power, relative power, coherence, and symmetry.

5. The method of claim 1, wherein said theta frequency band comprises a second set of univariate measurements selected from the group consisting of absolute power, relative power, coherence, and symmetry.

6. The method of claim 1, wherein said alpha frequency band comprises a third set of univariate measurements selected from the group consisting of absolute power, relative power, coherence, and symmetry.

7. The method of claim 1, wherein said beta frequency band comprises a fourth set of univariate measurements selected from the group consisting of absolute power, relative power, coherence, and symmetry.

8. A method for determining medication efficacy, comprising:
 a) providing;
  i) a patient having a physiologic brain imbalance, wherein said imbalance is identified using a first electroencephalography recording; and
  ii) a medication;
 b) converting said first electroencephalography recording to at least one first multivariate outcome measurement wherein said first outcome measurement comprises a plurality of first univariate Z scores, wherein said first multivariate outcome measurement is derived from a frequency band selected from the group consisting of ranging from approximately 0.5-3.5 Hertz, ranging from approximately 3.5-7.5 Hertz, ranging from approximately 7.5-12.5 Hertz, and ranging from approximately 12.5-35 Hertz;
 c) administering said medication to said patient, thereby resulting in a medicated patient;
 d) obtaining a second electroencephalography recording from said medicated patient and converting said second electroencephalography recording to at least one second multivariable outcome measurement wherein said second outcome measurement comprises a plurality of second univariate Z scores, wherein said second multivariate outcome measurement is derived from a frequency band selected from the group consisting of ranging from approximately 0.5-3.5 Hertz, ranging from approximately 3.5-7.5 Hertz, ranging from approximately 7.5-12.5 Hertz, and ranging from approximately 12.5-35 Hertz; and
 e) comparing said first multivariate outcome measurement with said second multivariate outcome measurement wherein a differential change between said first and second measurement determines said medication efficacy.

9. The method according to claim 8, wherein said comparing further comprises using a reference database.

10. The method according to claim 8, wherein said difference between said first multivariate outcome measurement and second follow-up multivariate outcome measurement is proportional to the efficacy of said medication.

\* \* \* \* \*

UNITED STATES PATENT AND TRADEMARK OFFICE
CERTIFICATE OF CORRECTION

| | | |
|---|---|---|
| PATENT NO. | : 7,754,190 B2 | Page 1 of 1 |
| APPLICATION NO. | : 10/602077 | |
| DATED | : July 13, 2010 | |
| INVENTOR(S) | : Stephen C. Suffin and W. Hamlin Emory | |

It is certified that error appears in the above-identified patent and that said Letters Patent is hereby corrected as shown below:

On the title page item (75), should read:

INVENTORS: Stephen C. Suffin and W. Hamlin Emory

Signed and Sealed this

Third Day of August, 2010

David J. Kappos
*Director of the United States Patent and Trademark Office*